(12) United States Patent
Roe et al.

(10) Patent No.: US 7,955,271 B2
(45) Date of Patent: Jun. 7, 2011

(54) TAPE TRANSPORT LANCE SAMPLER

(75) Inventors: Steven N. Roe, San Mateo, CA (US); Terry Beaty, Indianapolis, IN (US); Uwe Kraemer, Ilvesheim (DE); Volker Zimmer, Laumersheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 398 days.

(21) Appl. No.: 11/549,302

(22) Filed: Oct. 13, 2006

(65) Prior Publication Data

US 2008/0103415 A1 May 1, 2008

(51) Int. Cl.
*A61B 5/00* (2006.01)
*C12Q 1/00* (2006.01)

(52) U.S. Cl. .......................... 600/583; 435/4

(58) Field of Classification Search .................. 600/573, 600/575, 583–585; 606/181–183; 29/741, 29/742, 748, 749, 827
See application file for complete search history.

(56) References Cited

U.S. PATENT DOCUMENTS

| | | | |
|---|---|---|---|
| 2,896,628 A | 7/1959 | Speelman | |
| 2,989,212 A | 6/1961 | Ekenstam et al. | |
| 3,039,652 A | 6/1962 | Ekenstam et al. | |
| 3,835,992 A | 9/1974 | Adams, IV | |
| 4,123,840 A | 11/1978 | Rumer, Jr. | |
| 5,420,016 A | 5/1995 | Boguslaski et al. | |
| 5,514,152 A * | 5/1996 | Smith | 606/182 |
| 5,571,132 A | 11/1996 | Mawhirt et al. | |
| 5,591,139 A | 1/1997 | Lin et al. | |
| RE35,803 E | 5/1998 | Lange et al. | |
| 6,071,294 A | 6/2000 | Simons et al. | |
| 6,419,661 B1 | 7/2002 | Kuhr et al. | |
| 6,939,312 B2 | 9/2005 | Hodges et al. | |
| 7,297,122 B2 * | 11/2007 | Boecker et al. | 600/583 |
| 7,299,081 B2 | 11/2007 | Mace et al. | |
| 2003/0018282 A1 | 1/2003 | Effenhauser et al. | |

(Continued)

FOREIGN PATENT DOCUMENTS

EP  0 280 347 A  8/1988

(Continued)

OTHER PUBLICATIONS

U.S. Appl. No. 11/326,422, filed Jul. 1, 2004, Roe.

(Continued)

*Primary Examiner* — Max Hindenburg
*Assistant Examiner* — Brian Szmal
(74) *Attorney, Agent, or Firm* — Woodard, Emhardt, Moriarty, McNett & Henry LLP

(57) ABSTRACT

A lancet-sampler system is configured to automatically remove a protective cover from a lancet and automatically unpack a test pad just prior to use. This minimizes the risk of injury and reduces the chance of cross-contamination between the lancet and the test pad. The lancet defines a capillary groove for drawing body fluid from the incision via capillary action and a sample transfer opening for collecting the fluid from the groove. A carrier tape is coupled to the lancet. The carrier tape includes a test pad for analyzing the fluid. The tape is folded around the test pad to form an airtight package. The test pad is located at a position to align with the sample transfer opening when the tape is unfolded. The protective cover covers a portion of the lancet, and when the tape is pulled, the protective cover is automatically pulled from the lancet.

30 Claims, 19 Drawing Sheets

U.S. PATENT DOCUMENTS

| | | | |
|---|---|---|---|
| 2003/0024811 A1* | 2/2003 | Davies et al. | 204/403.01 |
| 2003/0028125 A1 | 2/2003 | Yuzhakov et al. | |
| 2003/0083686 A1 | 5/2003 | Freeman et al. | |
| 2003/0143113 A2 | 7/2003 | Yuzhakov et al. | |
| 2003/0211619 A1 | 11/2003 | Olson et al. | |
| 2003/0212346 A1 | 11/2003 | Yuzhakov et al. | |
| 2004/0092842 A1 | 5/2004 | Boecker et al. | |
| 2004/0096959 A1 | 5/2004 | Stiene et al. | |
| 2004/0127819 A1 | 7/2004 | Roe et al. | |
| 2004/0186394 A1 | 9/2004 | Roe et al. | |
| 2004/0193072 A1 | 9/2004 | Allen | |
| 2004/0193202 A1 | 9/2004 | Allen | |
| 2004/0206636 A1* | 10/2004 | Hodges et al. | 205/792 |
| 2004/0236251 A1 | 11/2004 | Roe et al. | |
| 2005/0049522 A1 | 3/2005 | Allen | |
| 2005/0232815 A1* | 10/2005 | Ruhl et al. | 422/66 |
| 2005/0234368 A1 | 10/2005 | Wong et al. | |
| 2005/0245844 A1 | 11/2005 | Mace et al. | |
| 2005/0245845 A1 | 11/2005 | Roe et al. | |
| 2005/0245954 A1 | 11/2005 | Roe et al. | |
| 2005/0251064 A1 | 11/2005 | Roe | |
| 2005/0277881 A1* | 12/2005 | Sibbitt, Jr. | 604/110 |
| 2006/0106411 A1 | 5/2006 | Schraga et al. | |
| 2006/0174592 A1 | 8/2006 | Chan | |
| 2006/0216817 A1* | 9/2006 | Hoenes et al. | 435/287.2 |
| 2006/0229532 A1* | 10/2006 | Wong et al. | 600/583 |

FOREIGN PATENT DOCUMENTS

| | | |
|---|---|---|
| EP | 1 402 812 A1 | 3/2004 |
| WO | WO 98/14125 | 4/1998 |
| WO | WO 2004/066822 A | 8/2004 |
| WO | WO2005/104948 A1 | 11/2005 |
| WO | WO 2006/092281 A2 | 9/2006 |
| WO | WO 2007/147494 A2 | 12/2007 |

OTHER PUBLICATIONS

U.S. Appl. No. 11/537,791, filed Oct. 2, 2006, Calasso et al.
International Patent Application PCT/EP2006/001857 International Preliminary Report mailed Sep. 20, 2007.
International Patent Application PCT/EP2007/009069 International Search Report mailed Mar. 28, 2008.
International Application No. PCT/EP2007/008870 International Search Report and Written Opinion mailed May 8, 2008.

* cited by examiner

TAPE TRANSPORT LANCE SAMPLER

BACKGROUND

The present invention generally relates to a transport system for integrated sampling devices and more specifically, but not exclusively, concerns a system in which a sterility cap is automatically removed from a lancet-sampler and a technique for manufacturing the same.

The acquisition and testing of bodily fluids is useful for many purposes and continues to grow in importance for use in medical diagnosis and treatment, such as for diabetes, and in other diverse applications. In the medical field, it is desirable for lay operators to perform tests routinely, quickly, and reproducibly outside of a laboratory setting, with rapid results and a readout of the resulting test information. Testing can be performed on various bodily fluids and, for certain applications, is particularly related to the testing of blood and/or interstitial fluid. Performing home-based testing can be difficult for many patients, especially for patients with limited hand dexterity, such as the elderly or diabetics. For example, diabetics can sometimes experience numbness or tingling in their extremities, such as their hands, which can make self-testing difficult because they are unable to accurately position a test strip to collect the blood sample. In addition, wounds for diabetics tend to heal more slowly, and as a result, there is a desire to make incisions less invasive.

Recently, lancet integrated test strips have been developed in which a test strip is integrated with a lancet or other piercing means so as to form a single disposable unit. While these integrated units have somewhat simplified the collection and testing of fluid samples, there are still a number of issues that need to be resolved before a commercial unit can be implemented. One issue concerns maintaining the sterility of the lancet so as to minimize the risk of infection. In practice, conventional plastic or syringe-type caps that are used to maintain the sterility of typical lancets cannot be incorporated with lancet integrated test strips for several reasons. With typical syringe-type caps, the cap encapsulates the lancet, and the cap is removed by pulling or twisting the cap off the lancet. As noted before, diabetics as well as the elderly can experience hand dexterity problems. Consequently, the manual removal of the cap from the lancet without destroying or damaging the integrated device can be difficult or even practically impossible. As of yet, a commercially practical system for automatically removing the cap has not been developed.

Integrated systems have been proposed that utilized closed needles that are manufactured through conventional needle drawing techniques. However, these conventional drawing techniques for needles can be rather expensive. Other systems have been proposed in which closed needles are manufactured using a semiconductor manufacturing process in which layers of semiconductor material are layered to form a closed needle. However, manufacturing a closed needle in such a way can be expensive and is not well suited for high volume production. Still yet other integrated disposables have been proposed that utilize a modified version of a conventional lancet for lancing the skin.

There is a trend to make lancets and needles smaller or thinner so as to make less traumatic or less invasive incisions, which in turn makes self-monitoring less painful as well as promotes healing of the incision. However, due to their thinner nature, lancets are more prone to bending or are susceptible to other damage, especially when protective caps are removed. Further, the pulling or twisting action during cap removal can damage the test strip, like the delicate electrodes in an electrochemical type test strip, or can even result in the lancet being separated from the test strip.

Other difficulties arise when a thinner lancet is used in integrated disposables in order to reduce pain. Some integrated disposable designs have an open capillary channel or groove formed in the lancet that is used to draw via capillary action body fluid from the incision to the test area or chamber. These open capillary groove integrated disposables experience a number of difficulties in drawing fluid via capillary action when the lancet is thin. As should be already appreciated, capillary action occurs when the adhesion of a liquid, such as body fluid, to the walls of the capillary channel is stronger than the cohesive forces between the liquid molecules. Adhesion of the liquid to the walls of the capillary channel causes the edge of the liquid to move upwards in the channel, and the surface tension acts to hold the surface of the liquid intact, so instead of just the edges moving upward, the whole liquid surface is dragged upward in the channel. However, with the open capillary groove designs, one of the walls of the capillary channel is eliminated, thereby reducing the overall contact area between the walls of the capillary channel and the surface of the body fluid. This reduction in contact area between the capillary channel and the body fluid reduces the capillary force applied to the fluid. To compensate, open capillary groove integrated disposables typically require that the capillary groove is deep so that the opposing sidewalls of the groove provide sufficient contact area with the meniscus to draw the body fluid. However, when the thickness of the lancet is reduced in order to reduce pain associated with lancing, the groove becomes too shallow to draw the body fluid via capillary action.

Integrated disposable designs have been proposed in which the entire unit is sealed within a protective packet. However, these designs require the entire disposable unit to be sterilized at the same time, which results in a whole host of difficulties. Unfortunately, sterilization techniques for lancets, such as radiation, adversely affect the chemistry of the test strip. Hence, if left uncompensated, the accuracy of the test strip can be significantly hampered. To compensate for the changes that occur during sterilization, samples from sterilized lots are taken so that an adjustment or calibration value can be calculated for the lot. Moreover, certain desirable sterilization techniques for lancets are impractical when the lancet and test strip are combined together because these techniques tend to damage or even destroy components on the test strip. In addition, undesirable cross contamination can occur between the lancet and the test strip when sealed in the same protective packet. For instance, components of the test strip, such as chemicals, biological components, adhesives, and the like, can migrate within the packet onto the lancet, thereby possibly compromising the sterility of the lancet.

Thus, needs remain for further contributions in this area of technology.

SUMMARY

One aspect concerns a tape assembly that includes a lancet and a carrier tape. The lancet includes a lancet tip configured to lance tissue. A protective cover covers at least a portion of the lancet tip. The tape is coupled to the lancet and the protective cover. The tape has a slackened section between the lancet and the protective cover for allowing removal of the protective cover from the lancet tip when the tape is pulled.

Another aspect concerns a technique for assembling a tape assembly. A lancet is provided with a portion of the lancet covered with a protective cover. A slackened section of a tape is formed. The lancet and the protective cover are attached to the tape with the slackened section located between where the lancet and the protective cover are attached to the tape.

A further aspect relates to a technique for automatically removing a protective cover from a lancet. A tape assembly includes a tape and the lancet with the protective cover covering at least a portion of the lancet. The lancet and the protective cover are attached to the tape with a slackened section of the tape located between where the lancet and the protective cover are attached to the tape. The protective cover is pulled from the lancet by applying tension to the tape.

Still yet another aspect relates to a body fluid sampling device that automatically aligns a test pad with a sample collection opening. The device includes a lancet that is configured to lance an incision in tissue. The lancet defines a capillary groove configured to draw body fluid from the incision via capillary action and the sample transfer opening configured to collect the body fluid from the capillary groove. A carrier tape is coupled to the lancet. The carrier tape includes a test pad configured to analyze the body fluid. The tape is folded around the test pad, and the test pad is located at a position to align with the sample transfer opening when the tape is unfolded.

A further aspect concerns a lancet-sampler that includes a lancet. The lancet has a body and a lancet tip extending from the body configured to cut an incision in tissue. The lancet has opposing first and second sides. The lancet defines a groove in the first side that extends from the lancet tip to the body. A cover covers at least a portion of the groove over the first side to define an enclosed capillary channel configured to draw body fluid via capillary action. The groove has at least a segment that extends completely through the lancet from the first side to the second side.

Further forms, objects, features, aspects, benefits, advantages, and embodiments of the present invention will become apparent from a detailed description and drawings provided herewith.

DESCRIPTION OF THE SELECTED EMBODIMENTS

Figure 1:
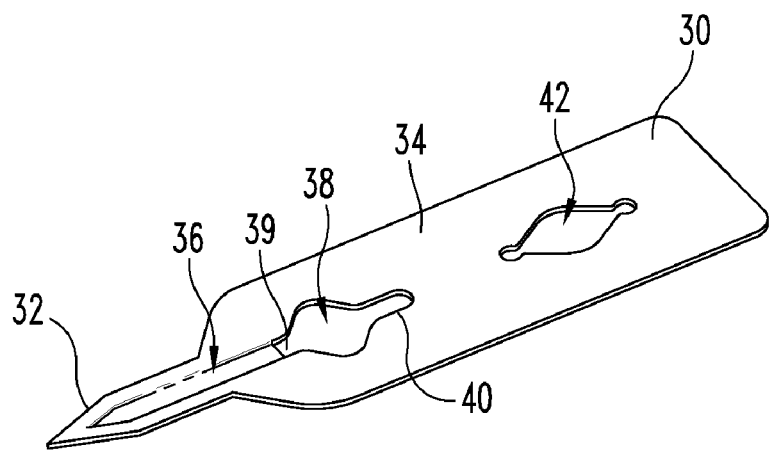
FIG. 1 is a perspective view of a lancet according to one embodiment.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. A number of embodiments of the invention are shown in detail, although it will be apparent to those skilled in the relevant art that some features that are not relevant to the present invention may not be shown for the sake of clarity. It should be noted that directional terms, such as "up", "down", "top", "bottom", "clockwise" and "counterclockwise", are used herein solely for the convenience of the reader in order to aid in the reader's understanding of the illustrated embodiments, and it is not the intent that the use of these directional terms in any manner limit the described, illustrated, and/or claimed features to a specific direction or orientation.

The present invention generally concerns a tape of lancet integrated test elements (LITs) and/or semi-integrated disposables as well as a technique for manufacturing the LITs and/or semi-integrated disposables. In particular, the tape includes a plurality of flat lancets. Each lancet includes a whole and/or half-etched capillary channel that connects to a sample transfer opening and an actuator engagement keyhole that is used to actuate the lancet. The capillary channel and the sample transfer opening are covered with a hydrophilic heat sealable foil via a continuous reel-to-reel process. Enclosing the capillary channel allows the lancet sampler to draw fluid via capillary action, especially when the lancet is thin. Afterwards, the individual lancets are punched from the strip. The tip of the lancet is heat-laminated between a foil sandwich, thereby forming a removable protective cover. Two strips of adhesive tape are attached to opposite ends of the lancet, and the lancet assembly is sterilized. A reagent label or test pad configured to analyze the fluid sample is applied to a main cassette or carrier tape. The cassette tape is folded over the test pad in a fanfold fashion, and the tape is secured over the test pad via a peelable adhesive to form an airtight package. In the package, a micro-desiccant bead can be affixed adjacent the test pad. The two strips of adhesive tape are attached to two opposite flaps or sections between the fold lines. During dispensing, the tape is pulled to unfold the package. As the tape unfolds, the protective cover is automatically pulled from the lancet tip. When fully unfolded, the test pad automatically aligns with the sample transfer opening. The lancet is then actuated to lance the skin, and the fluid is drawn onto the test pad via the channel in the lancet. The alignment of the test pad with the sample transfer opening can occur before or after the lancet lances the skin and collects the fluid. In other embodiments, the sample transfer opening is optional such that the fluid transfer occurs directly from the capillary channel.

With this system, the difficulties associated with the manual removal of the protective cap are eliminated because the system provides a unique technique for automatically removing caps. A number of the difficulties associated with sterilization are reduced because the lancet can be sterilized separately from the test pad. Moreover, the risk of cross-contamination between the lancet and the test pad is reduced because the lancet and test pad are only exposed immediately prior to use. As will be understood from the discussion below, the system also helps to alleviate a number of other issues. Although the present invention will be discussed with reference to collecting blood from the skin, it should be recognized that other types of body fluids, such as interstitial fluid, can be analyzed from various types of tissues, in addition to skin.

A perspective view of a lancet 30, according to one embodiment, used in the LIT is shown in FIG. 1. The lancet 30 in one form is made from surgical grade stainless steel, but it should be appreciated that the lancet 30 can made of other materials suitable for lancets. In one particular form, the lancet 30 is made from 76 μm thick precipitation hardening (PH) 17-7 stainless steel. As can be seen, the lancet 30 includes a lancet tip 32 that extends from a lancet body or base 34. The lancet tip 32 is configured to cut an incision in tissue. In the illustrated embodiment, the lancet tip 32 has a triangular shaped cutting edge, but it should be recognized that the tip 32 can be shaped differently in other embodiments. The profile of the lancet 30 in FIG. 1 is generally flat, which in turn simplifies packaging of the LIT. However, it is contemplated that the lancet 30 in other embodiments does not necessarily need to be flat.

Stretching from the lancet tip 32 to the lancet base 34, the lancet 30 has a capillary groove 36 that is used to transport a body fluid sample from an incision to a sample transfer opening or pooling area 38 in the lancet 30. In the illustrated embodiment, the capillary groove 36 extends partially through the lancet 30, and the sample transfer opening 38 extends completely through the lancet 30. Instead of being partially etched through the lancet 30, the capillary groove 36 in other embodiments can be a fully-etched capillary channel that extends completely through the lancet 30. As a side note, the terms "etched", "partially etched", and "fully etched" are being used so that the reader easily comprehend the discussed concepts, and it should be understood that the use of these terms in no way limits how the various grooves, openings, and other features are created. Although these features can be etched, it should be recognized that these features can also be created using other techniques as well, like stamping, cutting, and punching, to name a few examples. In one embodiment where the lancet 30 is 76 μm thick, the partially etched section of the capillary groove 36 has a width of approximately 250 μm and a depth of approximately 40 μm, but it should be recognized that the dimensions can vary in other embodiments. The sample transfer opening 38 is generally wider than the capillary groove 36 so as to collect the fluid from the capillary groove 36 for deposition onto a test pad. In the depicted embodiment, the sample transfer opening 38 has an oblong or elliptical shape, but the sample transfer opening 38 can be shaped differently in other embodiments or eliminated completely.

Between the capillary groove 36 and the sample transfer opening 38, the lancet 30 has a fully-etched section 39 that has generally the same width as the capillary groove 36, but the section 39 is fully etched like the sample transfer opening 38. If the fluid from the capillary groove 36 was directly transferred to the wider and fully etched sample transfer opening 38, the fluid flow might on occasion stop because fluid tends to have a higher affinity for smaller capillary channels, which in this case would be the capillary groove 36. The fully-etched section 39 before the sample transfer opening 38 provides a gradual transition that allows the momentum of the body fluid to carry the fluid to the sample transfer opening 38. Opposite the capillary groove 36, the sample transfer opening 38 has a vent slot 40 for venting air as the sample transfer opening 38 fills with fluid. In the illustrated embodiment, the sample transfer opening 38 is wider than the vent slot 40, but it is contemplated that the vent slot 40 can have the same width or be wider than the sample transfer opening 38 in other embodiments. Moreover, the vent slot 40 in further embodiments can be eliminated such that uncovered portions of the capillary groove 36 and/or the sample transfer opening 38 can vent air. In the base 34, the lancet 30 has an actuator engagement opening or keyhole 42 to which an actuator of a lancing mechanism engages in order to fire the lancet 30. In the depicted embodiment, the actuator engagement hole 42 includes an oblong-shaped central portion and opposing circular-shaped holes. As should be recognized, the actuator engagement hole 42 can be shaped differently in other embodiments.

Figure 2:
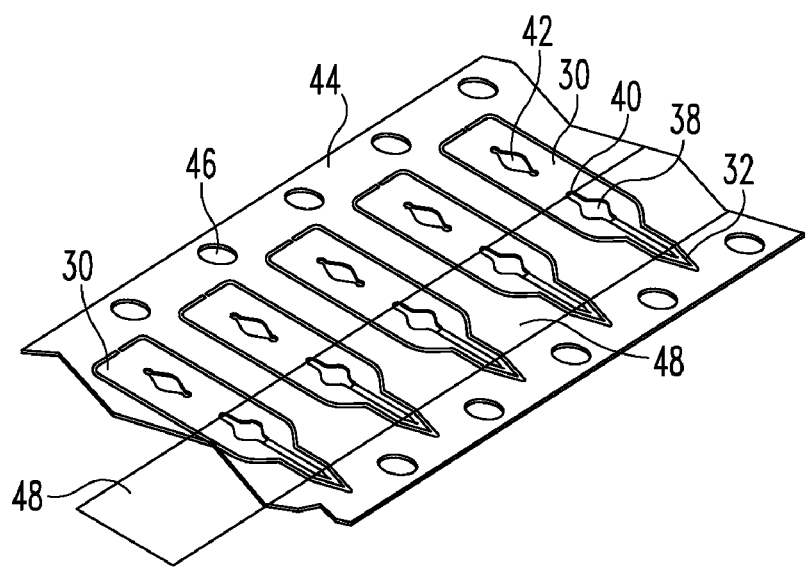
FIG. 2 is a perspective view of a lancet strip from which the FIG. 1 lancet is formed.
Figure 3:
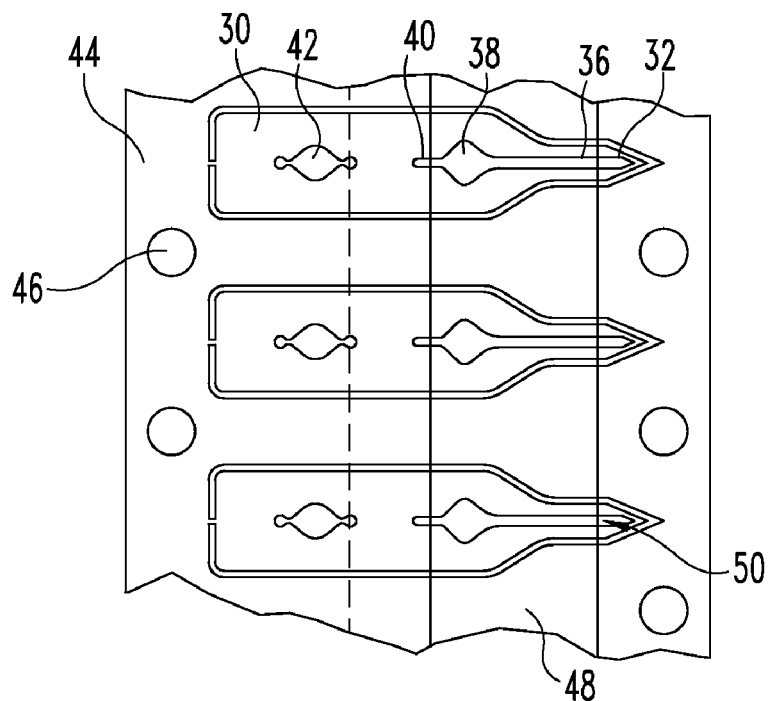
FIG. 3 is a top view of the FIG. 2 lancet strip.

Turning to FIGS. 2 and 3, the lancets 30 in one form are manufactured via a continuous reel-to-reel process in which the various features of the lancets 30 are formed from a continuous lancet strip 44. For example, the openings 38, 42 as well as the capillary groove 36 can be formed via photolithography, punching, and/or stamping techniques, to name a few examples. In one particular example, the capillary groove 36 is formed via photolithography by only partially etching into the lancet 30. As should be recognized, other types of manufacturing processes can be used to form the lancets 30. In the illustrated embodiment, the lancet strip 44 includes tractor openings 46 for indexing the lancet strip 44 during manufacturing, but the tractor openings 46 can be optional in other embodiments.

As mentioned before, it is desirable to have the lancet 30 as thin as possible so as to minimize pain associated with lancing. It was, however, discovered that when the thickness of the lancet 30 is reduced, the available depth of the opposing walls of the capillary channel 36 is likewise reduced. This reduced wall depth of the capillary channel 36 in turn reduces the capillary affinity of the channel 36 to such an extent that the capillary channel 36 would not be able to consistently draw fluid in sufficient amounts for testing purposes or practically draw any fluid up to the sample transfer opening 38.

Contrary to conventional wisdom that teaches the use of lancets with open capillary channels, the capillary groove or channel 36 of the lancet 30 in the illustrated embodiment is closed. To enhance the capillary action in thinner lancets, a cover foil 48 is used to enclose the capillary groove 36 so as to increase the contact area of the meniscus of the body fluid with the capillary groove 36. After the capillary groove 36 and sample transfer opening 38 are formed, the lancet strip 44 is laminated with the cover foil 48 to create an enclosed capillary channel 50. Laminating the cover foil 48 over the lancet 30 provides an easy technique to create a closed capillary channel. The cover foil 48 in one embodiment is heat sealed to the lancet strip 44, but the cover foil 48 in further embodiments can be secured in other manners, such as via a room temperature adhesive. In one form, the cover foil 48 is hydrophilic by being coated with a hydrophilic layer of material. However, it should be appreciated that the cover foil 48 can be made hydrophilic in other manners, and all or part of the cover foil 48 can be hydrophilic. The cover foil 48 in one form is hydrophilic before the cover foil 48 is attached to the lancet 30. In another form, hydrophilic material is deposited on a section the cover foil 48 that covers the capillary groove 36. Surfactants, which are typically used to make materials hydrophilic, tend to be slippery. The slippery nature of surfactants can make the attachment of the cover foil 48 to the lancet 30, with for example an adhesive, very difficult. To address this attachment issue, the cover foil 48 in one embodiment is not covered with a surfactant before the foil 48 is attached to the lancet 30. Rather, once the cover foil 48 is attached, a solution of alcohol and surfactant is poured, sprayed, and/or otherwise drawn into the now enclosed capillary channel 50. The solution is then dried to leave surfactant in the enclosed capillary channel 50. In one particular form, the cover foil 48 is a hydrophilic heat sealable 12 µm thick polyethylene terephthalate (PET) foil. In selected embodiments, all or part of the cover foil 48 can be transparent and/or semi-opaque so as to be able to detect fluid fill sufficiency.

As can be seen, most of the capillary groove 36 and the sample transfer opening 38 are covered by the cover foil 48 to form the enclosed capillary channel 50. However, a portion of the capillary groove 36 at the lancet tip 32 is left exposed so that the capillary channel 50 is able to collect the fluid sample. In a similar fashion, a portion of the vent slot 40 is open to the outside environment to permit venting of air from the capillary channel 50. In comparison to open capillary channel designs, it has been found that the enclosed capillary channel 50 tends to be more robust than open capillary channel systems. It is theorized that, by being enclosed, the capillary channel 50 can enhance the capillary action that is used to draw the fluid sample. Moreover, in contrast to open capillary channel designs that allow fluid to escape, the enclosed capillary channel 50 tends to reduces fluid waste, which in turn reduces the amount of body fluid needed for fluid collection. Nevertheless, it should be recognized that selected features from the system described herein can be adapted to other systems that have an open capillary channel design.

Figure 4:
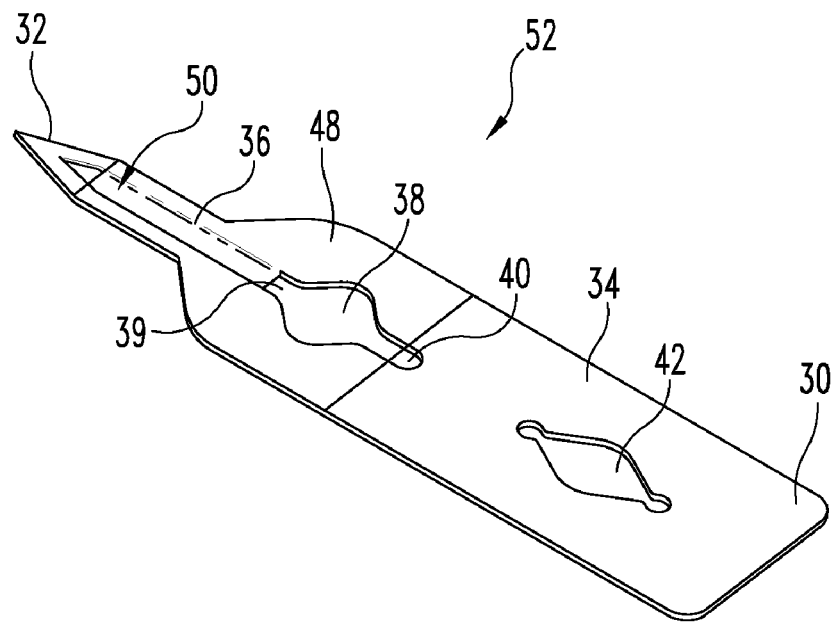
FIG. 4 is a perspective view of a lancet-sampler that incorporates the FIG. 1 lancet.

Referring to FIG. 4, subsequent to lamination of the cover foil 48 over the strip 44, the lancet 30 is punched from the strip 44 to form a lancet-sampler 52. In one form, the lancet-sampler 52 is punched from the strip 44 with a high-speed rotary male/female die system. However, it should be appreciated that the lancet-sampler 52 can be removed from the strip 44 in other manners.

Figure 5:
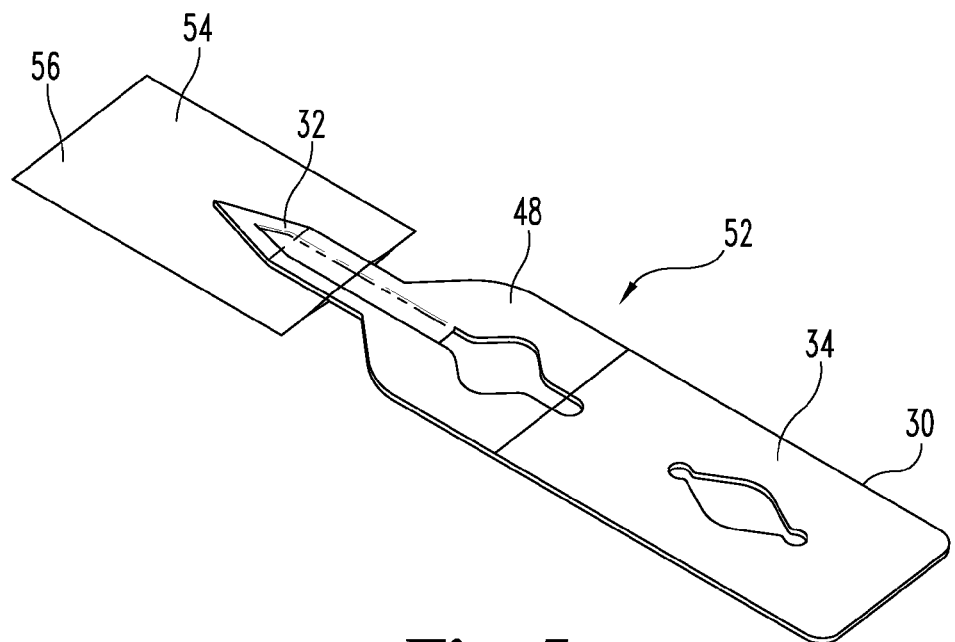
FIG. 5 is a perspective view of the FIG. 4 lancet-sampler with a protective cover covering one end of the lancet-sampler.

Looking at FIG. 5, all or a portion of the lancet tip 32 is sandwich between a protective foil or film 54 that is laminated together to form a protective tip or cover 56 for preventing injury as well as for maintaining the sterility of the lancet 30. In one form, the protective foil 54 is heat laminated together to form the protective cover 56, but it should be understood that the protective foil 54 can be laminated together in other manners, such as with an adhesive. As will be explained in greater detail below, the protective cap is configured to be automatically pulled off the lancet tip 32 before use. The protective foil 54 in one embodiment is a polyethylene (PE) or PET foil, but it is envisioned that other materials can be used. It also should be recognized that the protective cover 56 can be formed before the lancet-sampler 52 is punched from the strip 44. For instance, the lancet 30 can be bent or cut away from the strip and the protective foil 54 applied before the lancet-sampler 52 is punched from the strip 44.

Figure 6:
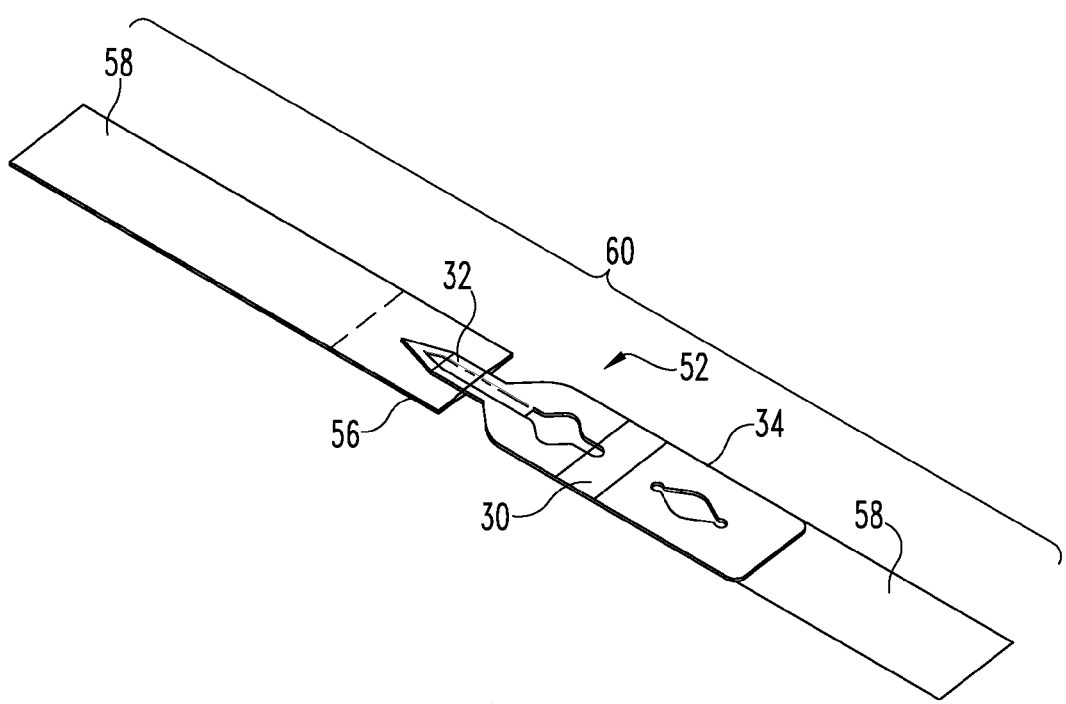
FIG. 6 is a perspective view of a lancet-sampler label that incorporates the FIG. 4 lancet-sampler.

Once the protective cover 56 covers the lancet tip 32, connector tapes 58 are secured at opposite ends of the lancet-sampler 52 to create a lancet-sampler label 60, as is depicted in FIG. 6. The tape connectors 58 are used to secure the lancet-sampler 52 to a carrier or cassette tape. In the illustrated embodiment, the connector tapes 58 are adhesive tapes, and in one particular form, the connector tapes 58 include PET adhesive tape. One of the connector tapes 58 is secured to protective cover 56, and the other connector tape 58 is secured to the base 34 of the lancet 30. As viewed in FIG. 6, the connector tapes 58 are secured to the top side of the lancet-sampler 52, but it should be appreciated that the connector tapes 58 can be secured elsewhere. For example, one of the connector tapes 58 can be secured to the top side of the lancet-sampler 52, and the other can be secured to the bottom side of the lancet-sampler 52. In another example, the connector tapes 58 can be attached along the edges of the lancet-sampler 52. As should be recognized, one or more of the connector tapes 58 can be made integral with the lancet-sampler 52 or the connector tapes 58 can be eliminated. For instance, one of the connector tapes 58 can be integrally formed with the protective cover 56. Once assembled, the lancet-sampler label 60 is then sterilized. In one form, the lancet-sampler label 60 is sterilized using an inline electron beam (e-beam) sterilization process. Nevertheless, the lancet 30 can be sterilized in other manners, such as via gamma radiation or ultraviolet sterilization techniques. Moreover, it should be appreciated that the lancet 30 can also be sterilized at the various assembly stages before the connector tapes 58 are attached to the lancet-sampler 52.

Figure 7:
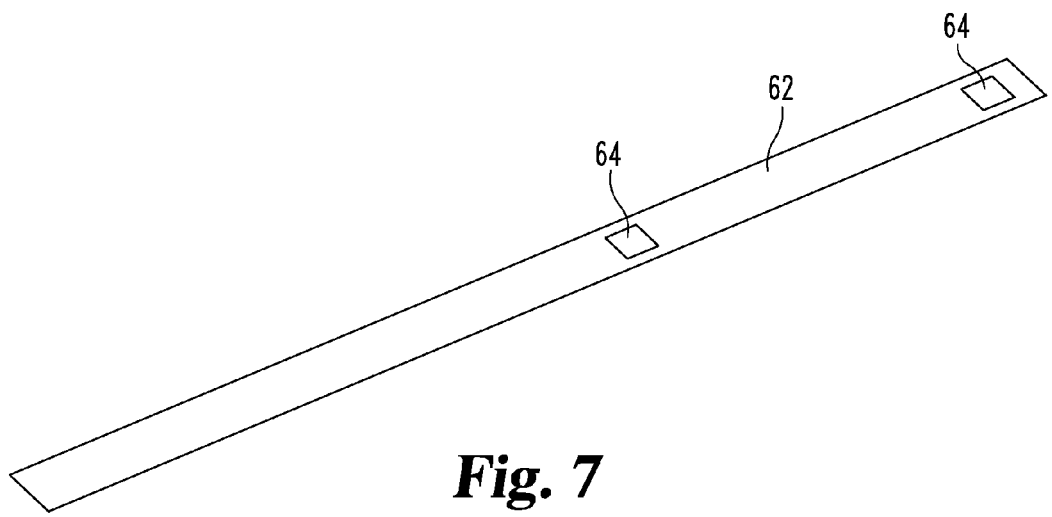
FIG. 7 is a perspective view of a carrier tape to which the FIG. 6 lancet-sampler label is attached.

As noted above, the connector tapes 58 are used to secure the lancet-sampler label 60 to a cassette tape. By being disposed on the tape, multiple lancet-samplers 52 can be used in a cassette or other type of device that can perform multiple tests before requiring disposal. It, however, is contemplated that features of this system can be incorporated into single use meters. FIG. 7 illustrates a carrier or cassette tape 62, according to one embodiment, to which one or more of the lancet-sampler labels 60 are secured. As depicted, one or more reagent labels or test pads 64 for analyzing the fluid sample is applied to the tape 62. In one embodiment, the tape 62 is a 5 mm wide×0.012 mm thick PET cassette tape, but it is envisioned that the tape 62 in other embodiments can be dimensioned differently and made from other materials. For instance, the tape 62 in another form is 23 µm thick. The test pad 64 incorporates the chemistry and/or sensors used to analyze a fluid sample. In one form, the test pad 64 is configured for electrochemical analysis of a fluid sample. The test pad 64 can for example include electrodes, such as working, counter, and reference electrodes, and chemistry, like mediators and enzymes, for electrochemically analyzing a fluid sample. Any number of electrochemical techniques can be used to analyze a fluid sample, such as amperometric, potentiometric, and coulometric techniques, to name a few. In other forms, the test pad 64 can have chemistry for analyzing a fluid sample optically, such as through reflective and/or transmissive techniques. As should be appreciated, the test pad 64 can be configured to analyze the fluid sample in other manners as well.

Figure 8:
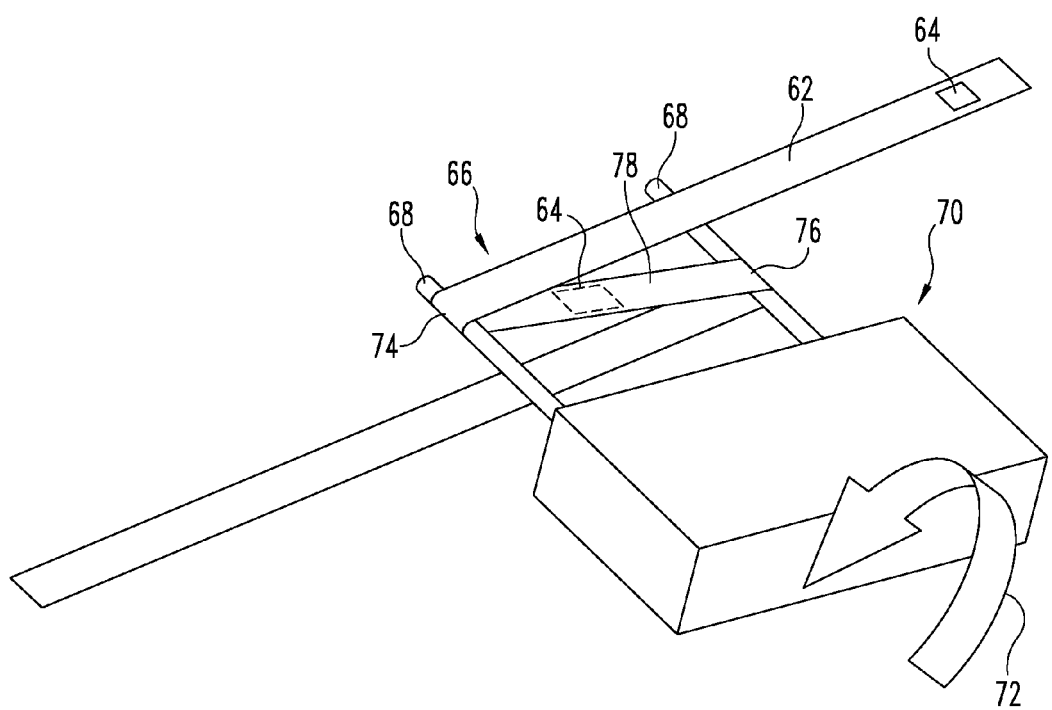
FIG. 8 is a perspective view of the FIG. 7 carrier tape during folding.

To facilitate automatic removal of the protective cover 56, the tape 62 has a slackened or loose section that provides enough slack so that the protective cover 56 is able to clear the lancet tip 32 when tension is applied to the tape 62. The slackened section of tape 62 also provides enough slack so that the lancet 30 can be fired to form an incision. Before the lancet-sampler label 60 is attached, the tape 62 is folded in a fanfold manner (180°) over the test pad 64, as is illustrated in FIG. 8. The folded section of the tape 62 forms a packet 66 for protecting the test pad 64 as well as provides the slack to allow the cap 56 to be pulled from the lancet 30. The packet 66 in one embodiment is sealed with a vapor tight pealing adhesive, and a micro-desiccant bead is affixed adjacent to the test pad 64 in order to control the humidity levels within the packet 66. In another embodiment, a packet 66 is not formed, but rather, the tape 62 is loosely folded in a manner to create loose loops or a slackened section of tape 62 around the test pad 64. In this embodiment, the cassette in which the tape 62 is housed contains a desiccant and has seals to maintain humidity levels of the test pad 64. As should be appreciated, this system can be adapted for use in non-integrated systems. For example, in still yet a further form, the tape 62 does not include the test pad 64, but rather, the lancet 30 is used to only form an incision (and not to collect and analyze a fluid sample). In this case, the tape 62 does not have the packet 66. Instead, the tape 62 has a slackened section between where the tape is attached to the protective cover 56 and the lancet 30 so as to facilitate the removal of the protective cover 56.

Returning to the FIG. 8 embodiment, a pair of fingers 68 of a folding mechanism 70 are used to fold the tape 62. As can be seen, the fingers 68 of the folding mechanism 70 engage opposite sides of the tape 62, and the mechanism 70 is rotated in a counterclockwise fashion, as indicated by arrow 72 in FIG. 8, in order to fold the tape 62 to form the packet 66. The fingers 68 form first 74 and second 76 creases or folds with an intermediate tape section 78 that has the test pad 64. As will be discussed in detail below, the distance between the first crease 74 and the test pad 64 is selected so that, once unfolded, the test pad 64 aligns with the sample transfer opening 38 in the lancet 30. This allows the test pad 64 to be positioned to directly absorb the fluid sample in the sample transfer opening 38. The intermediate section 78 with the test pad 64 is folded against the tape 62 and sealed to form the packet 66. Once the tape 62 is folded, the fingers 68 are temporarily pulled away from the tape 62 as the tape 62 is indexed, and afterwards, the fingers 68 are reapplied to the tape 62 to fold the next packet 66. As should be appreciated, the folding mechanism 70 allows the tape 62 to be folded in a continuous process, which in turn simplifies manufacturing. It, however, should be appreciated that the tape 62 in other embodiments can be folded in other manners, such as manually or with a different type of folding mechanism.

Figure 9:
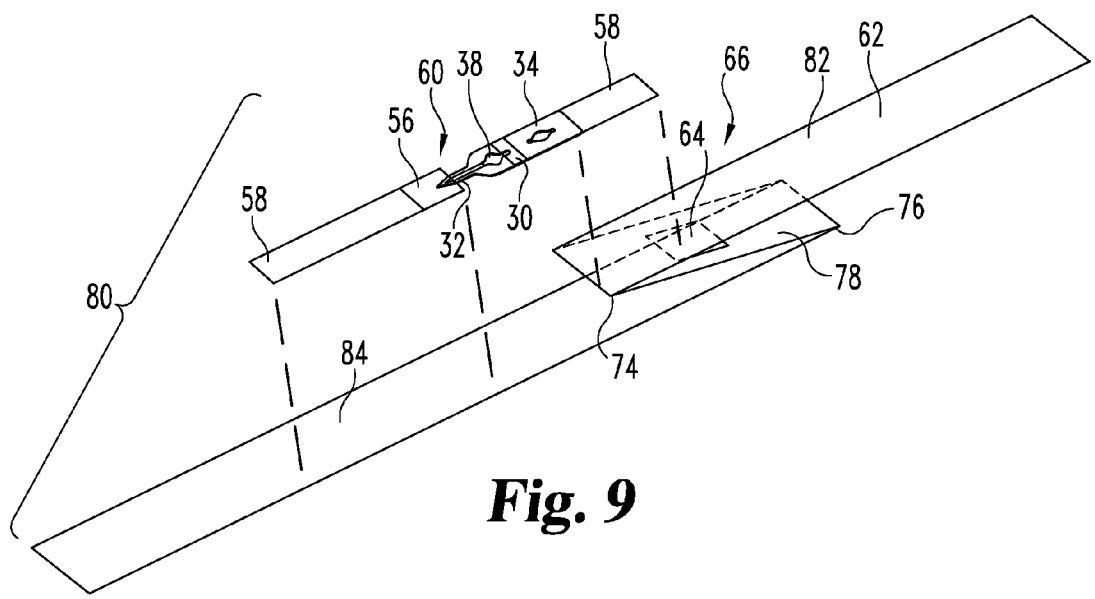
FIG. 9 is an exploded view of a tape assembly that includes the FIG. 6 lancet-sampler and the FIG. 7 carrier tape.
Figure 10:
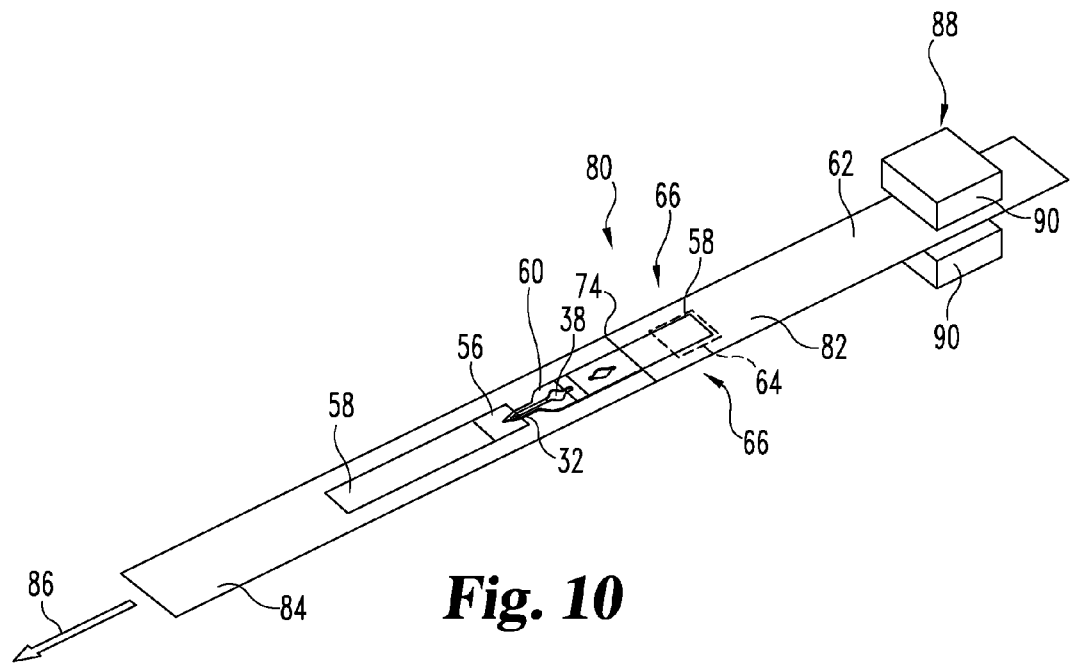
FIG. 10 is a perspective view of the FIG. 9 tape assembly.

Looking at FIGS. 9 and 10, the lancet-sampler label 60 is attached to the tape 62 via the connector tapes 58 such that the lancet-sampler label 60 spans across the first crease 74 to form a tape assembly 80. The lancet-sampler labels 60 can be secured to the tape 62 in a variety of manners, such as via an adhesive, welded, and/or bonded. In particular, the connector tape 58 that is secured to the base 34 of the lancet 30 is attached to a first section 82 of the tape 62, which is upstream from the first crease 74, and the connector tape 58 that is secured to the protective cover 56 is attached to a second section 84 of the tape 62, which is downstream from the intermediate section 78 and the second crease 76. Since the lancet-sampler label 60 is attached to the tape 62 after sterilization, the harmful effects to the test pad 64 from sterilization are avoided. In turn, this avoids the need for recalibration of the tape assembly 80.

Once assembled, the tape assembly 80 in one embodiment is housed within a cassette. For example, the tape assembly 80 can be stored in cassettes like those illustrated and described in U.S. patent application Ser. No. 11/326,422, filed Jan. 5, 2006, entitled "Lancet Integrated Test Element Tape Dispenser", which is hereby incorporated by reference in its entirety. In one form, an unused section of the tape assembly 80 is stored in a stacked manner within a supply portion of the cassette so as to reduce the chance of bending of the lancets 30, which can result in damage to the lancets 30. After use, the used section of the tape assembly 80 can be wrapped around a spool within a waste portion of the cassette because damage to the lancets 30 after use is not a concern. If needed, the cassette can include a desiccant and seals to maintain low humidity levels within the cassette so as to preserve the test pads as well as other components. It is envisioned that the tape assembly 80 can be stored in other manners. By way of non-limiting examples, the tape assembly 80 can be stored in magazines, discs, drums, and cartridges, to name a few.

As alluded to above, the tape assembly 80 is configured to automatically remove the protective cover 56 from the tip 32 of the lancet 30. Referring again to FIG. 10, the lancet-sampler label 60 is coupled to the first 82 and second 84 tape sections with the packet 66 in between. Before the lancet-sampler 52 is used, such as when the lancet-sampler 52 is initially indexed from a supply portion of a cassette, tension is applied to the second section 84 of the tape 62, as indicated by arrow 86 in FIG. 10. In one embodiment, the tension is applied via a spool around which the used section of tape 62 is wound after use. In another embodiment, the tension is applied via a tractor mechanism that is used to index the tape 62. It should be appreciated that the tape 62 can be tensioned in other manners. As the tension is applied, the first section 82 of the tape 62 is held fixed in place via a gripper or brake mechanism 88. The brake mechanism 88 includes opposing brake pads 90 that clamp against the tape 62 to hold the first section 82 in place. As should be recognized, the first section 82 of tape can be held in place in other manners. For instance, a spool or tractor mechanism can be used to hold the first section 82 in place. It is envisioned that in other embodiments tension can be applied to the tape 62 in other manners. For example, the first section 82 of the tape 62 can be pulled while the second section 84 is fixed in placed. In yet another example, both sections 82, 84 of the tape 62 are pulled in opposite directions at the same time.

Figure 11:
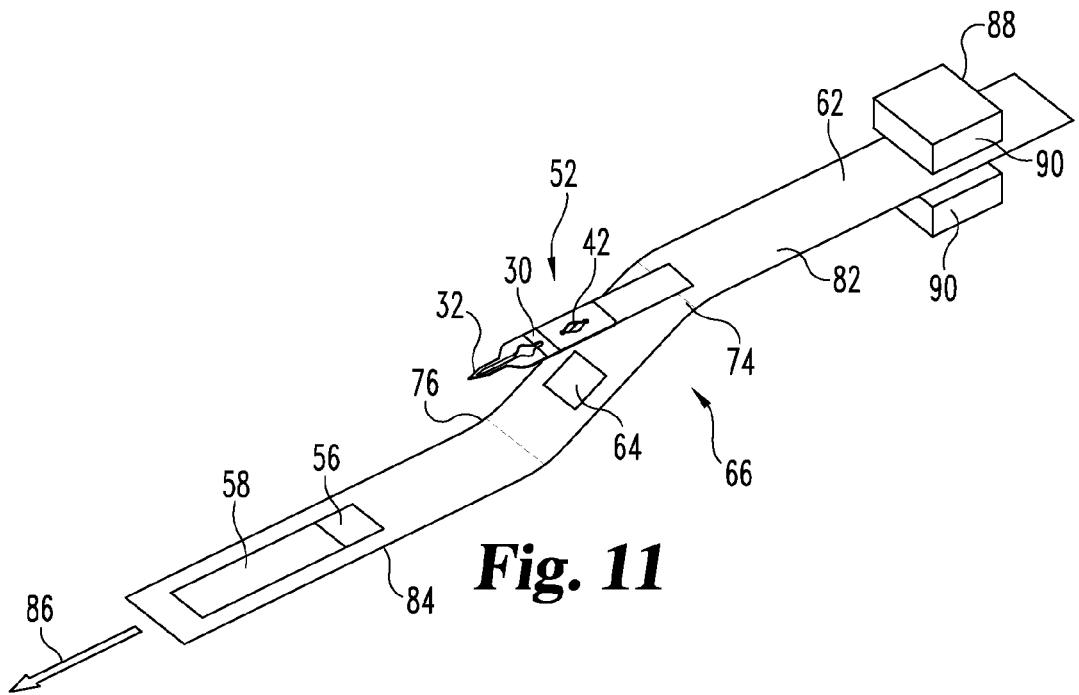
FIG. 11 is a first perspective view of the FIG. 9 tape assembly as the FIG. 7 carrier tape unfolds.

Turning to FIG. 11, as the tension is applied in direction 86, the protective cover 56 is pulled from the lancet 30, thereby exposing the lancet tip 32. After the protective cover 56 is removed, the lancet 30 can then be used to form an incision in tissue. Once the protective cover 56 is removed or some time thereafter, the brake mechanism 88 releases the tape 62 so that the tape 62 can be indexed. To form the incision, the firing mechanism engages the actuator engagement opening 42 so as to be able to fire the lancet 30 towards the tissue. As should be appreciated, the lancet 30 can be fired via various lancing mechanisms, like a spring-driven lancing mechanism, an electromechanical lancing mechanism, and the like. For example, a firing mechanism like the one described and illustrated in U.S. patent application Ser. No. 10/737,660, filed Dec. 16, 2003, which is herby incorporated by reference in its entirety, can be used to fire the lancet 30.

During or after the protective cover 56 is pulled away from the lancet 30, the folds forming the packet 66 containing the test pad 64 peel away from one another, as is depicted in FIG. 11. In one form, the peelable adhesive in the packet 66 releases, thereby opening the packet 66. In contrast to previous systems, the packet 66 is designed to keep the test pad 64 protected immediately prior to use, which in turn reduces the chance of cross-contamination between the lancet 30 and the test pad 64. As noted before, the packet 66 can be sealed in other manners, such as welded shut, or not sealed at all. In these other embodiments, the folds of the packet 66 can separate in other manners. For instance, the packet 66 in other embodiments can include weakened sections or break lines that break when tension is applied so as to allow the packet 66 to unfold. The free loop of tape 62 formed by the unfolded packet 66 provides freedom of movement for actuating the lancet 30 to form the incision. Lancing can occur before or after the packet 66 is completely unfolded.

Figure 12:
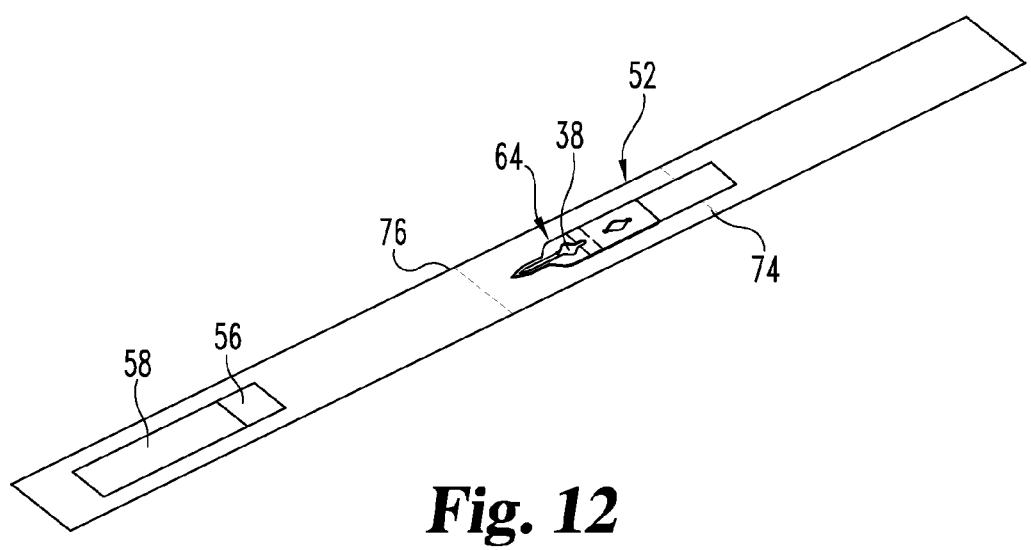
FIG. 12 is a second perspective view of the FIG. 9 tape assembly when the FIG. 7 carrier tape is completely unfolded.
Figure 13:
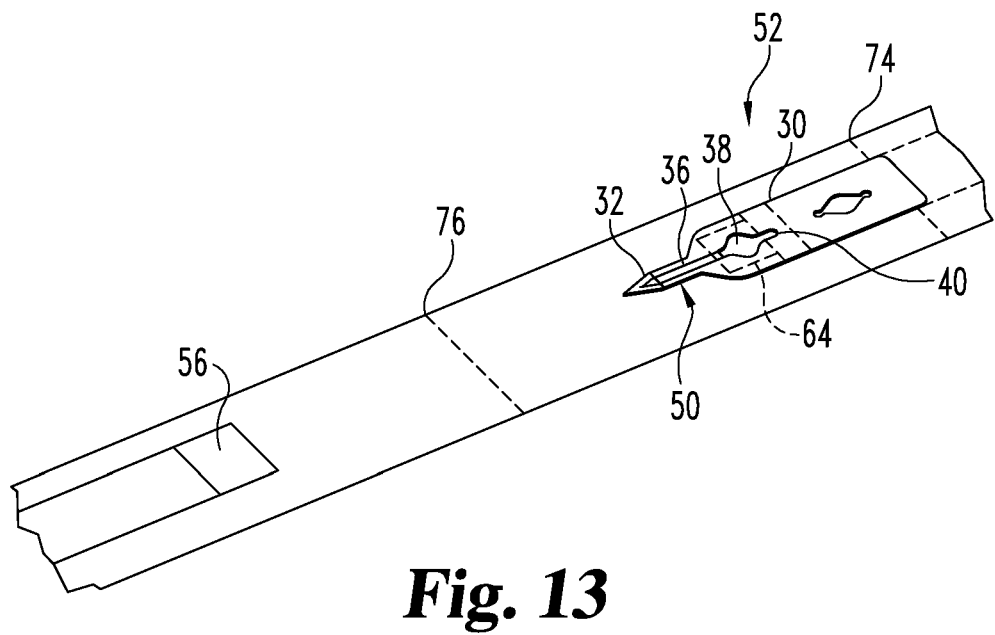
FIG. 13 is an enlarged view of the FIG. 9 tape assembly when the FIG. 7 carrier tape is completely unfolded.

Once the packet 66 is fully unfolded, the test pad 64 in FIGS. 12 and 13 is aligned directly underneath the sample transfer opening 38 so that the test pad 64 is able to directly receive the fluid sample from the sample transfer opening 38. It is envisioned that in other embodiments the packet does not necessarily need to be fully unfolded before the test pad 64 is aligned with the sample transfer opening 38.

The transfer of the fluid sample from the lancet 30 to the test pad 64 can occur in several ways. In one way, the lancet 30 first collects the fluid sample and then is subsequently moved over the test pad 64 as the packet 66 completely unfolds. For example, the incision is formed and the fluid is collected before the packet 66 is completely unfolded. In particular, the lancet 30 lances the skin or other tissue with the packet 66 only partially unfolded, such as in the manner illustrated in FIG. 11. Fluid collection can occur while the tip 32 of the lancet 30 is still located within the tissue (subcutaneously) or the fluid sample can be collected on the surface of the tissue. After the sample is drawn into the sample transfer opening 38, the packet 66 is completely unfolded so as to bring the test pad 64 into contact with the fluid sample within the sample transfer opening 38. The fluid is then transferred to the test pad 64 and subsequently analyzed. In another way, the packet 66 is completely unfolded before fluid collection occurs. For example, the packet 66 in one embodiment is completely unfolded, and the test pad 64 is positioned underneath the sample transfer opening 38 before the lancet 30 forms the incision and the fluid sample is collected with the capillary groove 36. It is contemplated that the transfer of the fluid sample can occur in other ways as well.

As mentioned before, the fluid sample can be collected subcutaneously or on the surface of the tissue. Regarding collection of fluid on the surface of the tissue, a number of techniques can be used to collect the sample. For instance, after forming the incision, the lancet-sampler 52 is temporarily retracted from the tissue, and once a predefined period has elapsed and/or fluid is detected on the surface of the tissue, the lancet-sampler 52 is reapplied to the incision in order to collect a fluid sample via the capillary channel 50. An electromechanical positioning system, such as disclosed in U.S. patent application Ser. No. 10/737,660, filed Dec. 16, 2003, entitled "Blood Acquisition Suspension System", which is hereby incorporated by reference, can be used to position the lancet-sampler 52. The electromechanical positioning mechanism slowly moves the lancet-sampler 52 towards the tissue until a fill sensor in the lancet-sampler 52 detects that a sufficient amount of fluid has been collected.

Figure 14:
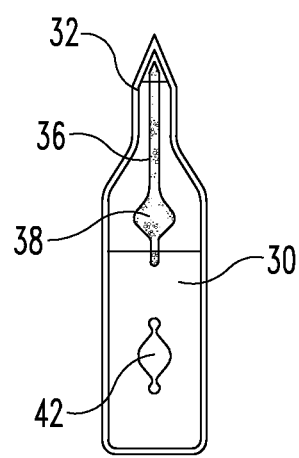
FIG. 14 is a top view of the FIG. 4 lancet-sampler when filled with a body fluid.

FIG. 14 shows an example of a fluid sample that has been collected with the lancet-sampler 52. As can be seen, the fluid from the lancet tip is drawn up the capillary groove 36 and into the sample transfer opening 38. As noted before, the cover foil 48 over the capillary groove 36 tends to enhance fluid collection. Once the fluid reaches the sample transfer opening 38, the fluid then can be immediately transferred to the test pad 64 or the lancet 30 can be moved so that the fluid can be transferred to the test pad 64. In one embodiment, the body fluid volume needed for analysis is 100 nanoliters (nL), and the test time is approximately 1-2 seconds. However, it is contemplated that other sample volumes can be used and test times can be different in other embodiments. Once the fluid sample is analyzed, the section of tape 62 containing the now used lancet-sampler 52 is wrapped around a waste spool in the cassette for later disposal. It should be recognized that the used lancet-samplers 52 can be disposed of in other manners.

Figure 15:
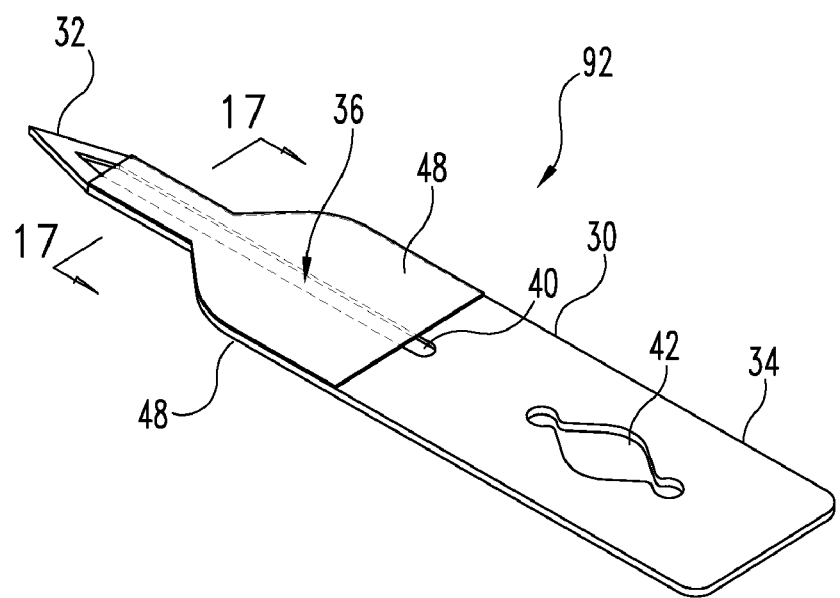
FIG. 15 is a perspective view of a lancet-sampler according to another embodiment.
Figure 16:
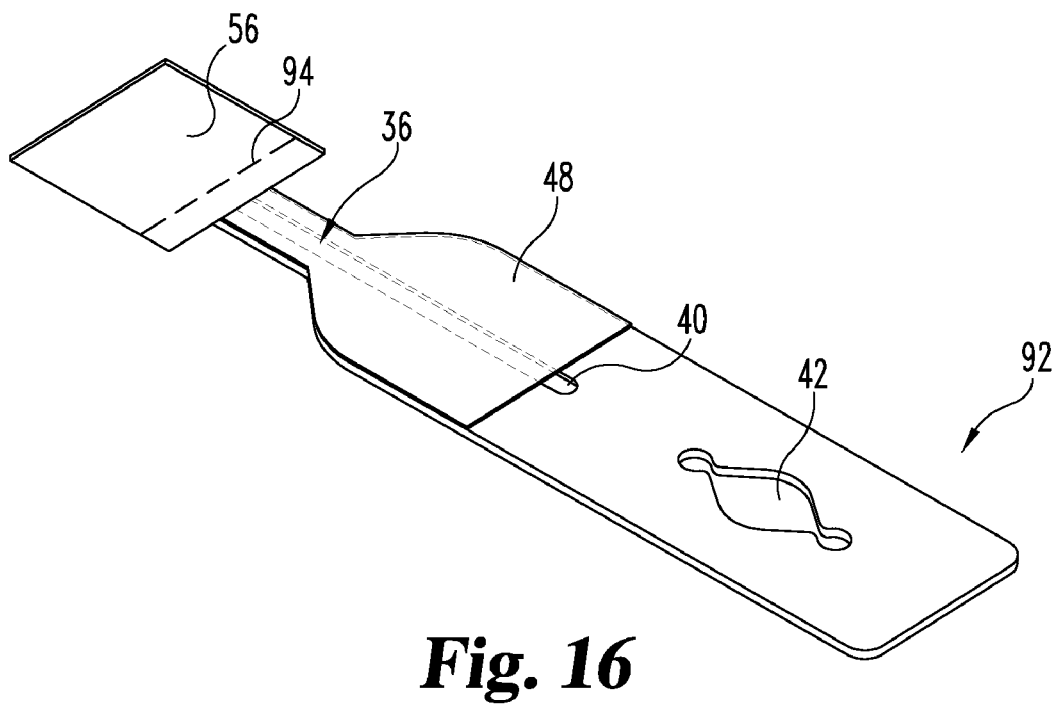
FIG. 16 is a perspective view of the FIG. 15 lancet-sampler with an end covered with a protective cover.
Figure 17:
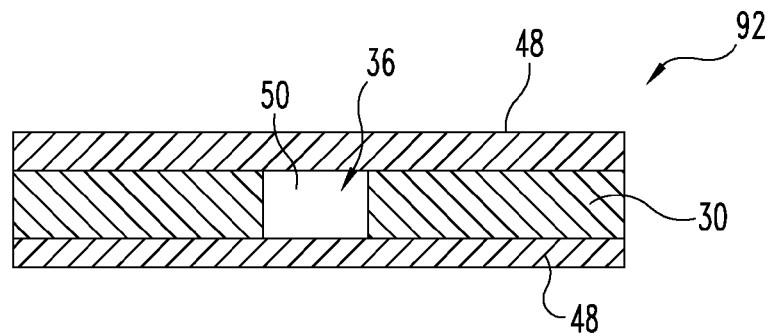
FIG. 17 is a cross sectional view of the FIG. 15 lancet-sampler as taken along line 17-17 in FIG. 15.

A lancet-sampler 92 according to another embodiment will be now described with reference to FIGS. 15, 16, and 17. As can be seen, the lancet-sampler 92 in FIG. 15 shares several features in common with the lancet-sampler 52 that was previously described with reference to FIG. 4. Like the previous embodiment, the lancet-sampler 92 includes the lancet 30 with the lancet tip 32 extending from the lancet body 34, the capillary groove 36, the vent slot 40, the cover foil 48, and the protective cap 56. For the sake of clarity as well as brevity, the commonly shared features will not be discussed at length below, but reference is made to the previous discussion of these features.

To protect the cover foil 48 when the protective cap 56 is pulled from the lancet tip 32, the protective cap 56 has a break line 94 that is scored, thinned, and/or otherwise weakened so that the protective cap 56 detaches from the lancet 30 at the break line 94. As should be appreciated, the break line 94 can be formed in any number of manners, such as by mechanically scoring the protective cap 56 or scoring with a laser, to name a few examples.

Figure 18:
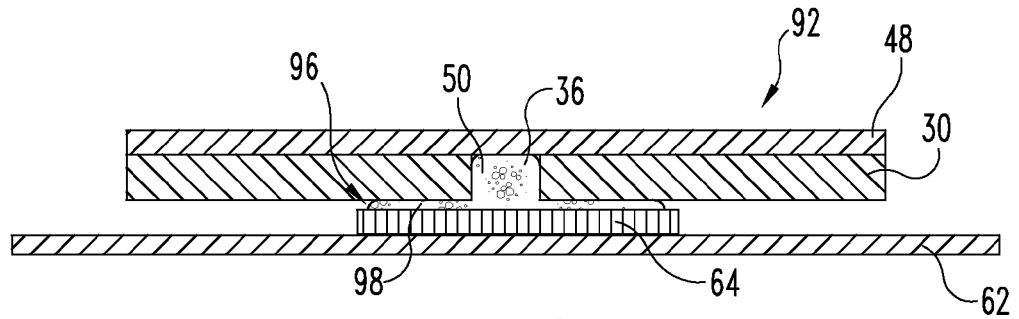
FIG. 18 is a cross sectional view of the FIG. 17 lancet sampler when fluid is transferred to a test pad on the tape.

In the illustrated embodiment, the lancet-sampler 92 does not have the sample transfer opening 38, but rather, the capillary groove 36 is used to directly deposit the sampled body fluid onto the test pads 64 on the tape 62. As illustrated in FIG. 15, the capillary groove 36 is fully etched through the lancet 30 along the entire length of the capillary groove 36. That is, the capillary groove 36 opens on both sides of the lancet 30. By being fully etched, the capillary groove 36 maximizes the available volume for transporting body fluid, which is helpful especially for thin lancets. Moreover, the fully etched capillary groove 36 tends to simply manufacturing because it eliminates the need tightly to control depth tolerances required to form a partially etched capillary groove 36. It is however envisioned that in other embodiments the capillary groove 36 can have sections that are partially etched. To form the enclosed capillary channel 50, the lancet 30 is sandwiched between a pair of cover foils 48, as is depicted in FIG. 17. In another variation, the capillary groove 36 is fully etched, but only one side of the capillary channel 50 is covered with a cover foil 48, such as shown in FIG. 18, thereby creating an open capillary channel configuration along the entire length of the capillary channel 50. The capillary channel 50 in still yet other embodiments can have sections that are open and other sections that are closed. Referring to FIG. 15, at the distal end of the lancet tip 32, the capillary groove 36 is uncovered or exposed so that the capillary groove 36 is able to collect body fluid from the incision, and the opposite end of the capillary groove 36 is exposed so as to form the vent slot 40.

Looking at FIG. 18, a section of the capillary groove 36 on the side of the lancet 30 that faces the test pad 64 is likewise not covered by the cover foil 48 so that the capillary groove 36 is able to deposit body fluid onto the test pad 64. Once the lancet-sampler 92 is positioned over the test pad 64, the lancet-sampler 92 and the carrier tape 62 (test pad 64) form a fluid transfer gap 96. In comparison to the capillary groove 36, the fluid transfer gap 96 has a higher affinity for the body fluid because the fluid transfer gap 96 is smaller than the capillary groove 36. Due to the higher affinity, the body fluid is transferred to the fluid transfer gap 96 such that the body fluid spreads below the lancet-sampler 92 and over the test pad 64. As can be seen, body fluid 98 in the fluid transfer gap 96 is able to cover an area that is wider than the capillary groove 36. It is contemplated that the lancet-sampler 92 and/or the carrier tape 62 can contain portions that are hydrophobic and/or hydrophilic so as to direct the fluid flow.

Figure 19:
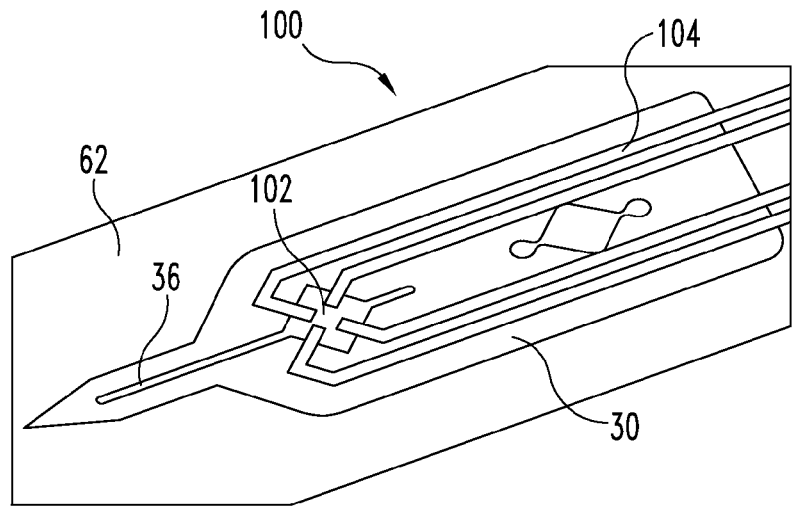
FIG. 19 is a perspective view of a lancet-sampler tape according to a further embodiment that is configured to analyze fluid samples electrochemically.

An electrochemical version of a lancet-sampler 100 according to still yet another embodiment is illustrated in FIG. 19. The lancet-sampler 100 in FIG. 19 shares several features in common with the previous embodiments, such as the lancet 30, the capillary groove 36, and the test tape 62. For the sake of clarity as well as brevity, the commonly shared features will not be discussed at length below, but reference is made to the previous discussions. The lancet-sampler 100 includes a reagent or test layer 102 with chemicals for electrochemically analyzing fluid samples, like enzymes and mediators. The reagent layer 102 is disposed on the carrier tape 62 and covers one or more electrodes 104. The electrodes 104 can include working, counter, and reference electrodes as well as other types of electrodes, such as for detecting fill sufficiency. The electrodes 104 are disposed on the carrier tape 62. All or portions of the electrodes can be disposed on the same side or on the opposite side of the carrier tape 62 as the reagent layer 102. In the illustrated embodiment, the electrodes 104 and reagent layer are disposed on the same side.

Figure 20:
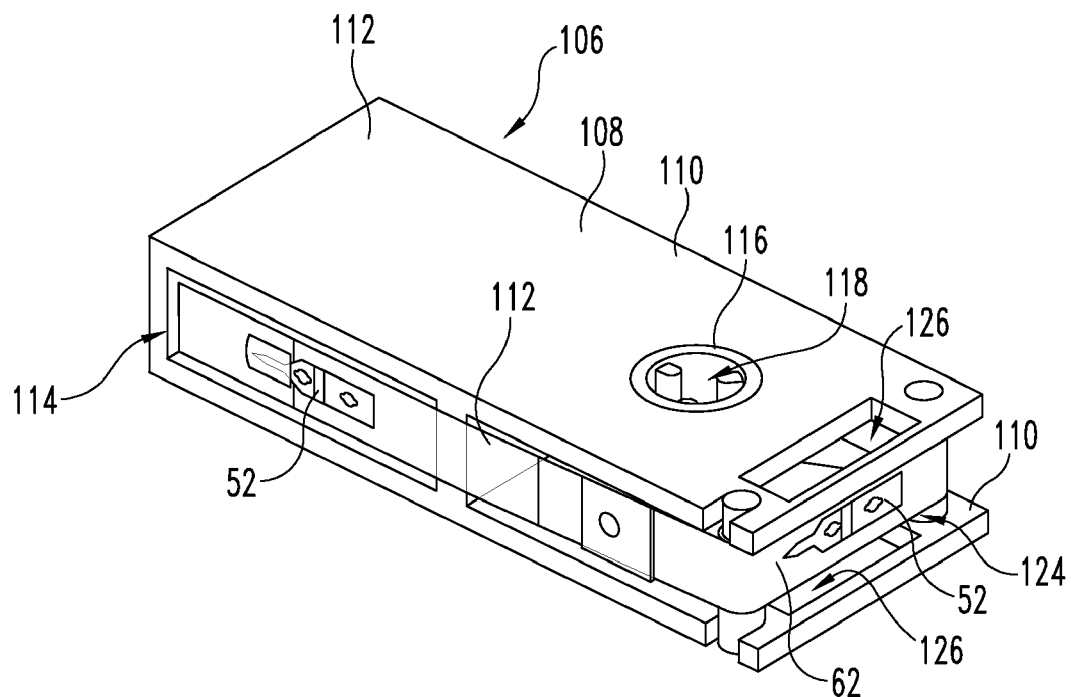
FIG. 20 is a perspective view of a cassette according to one embodiment in which the carrier tape can be stored.
Figure 21:
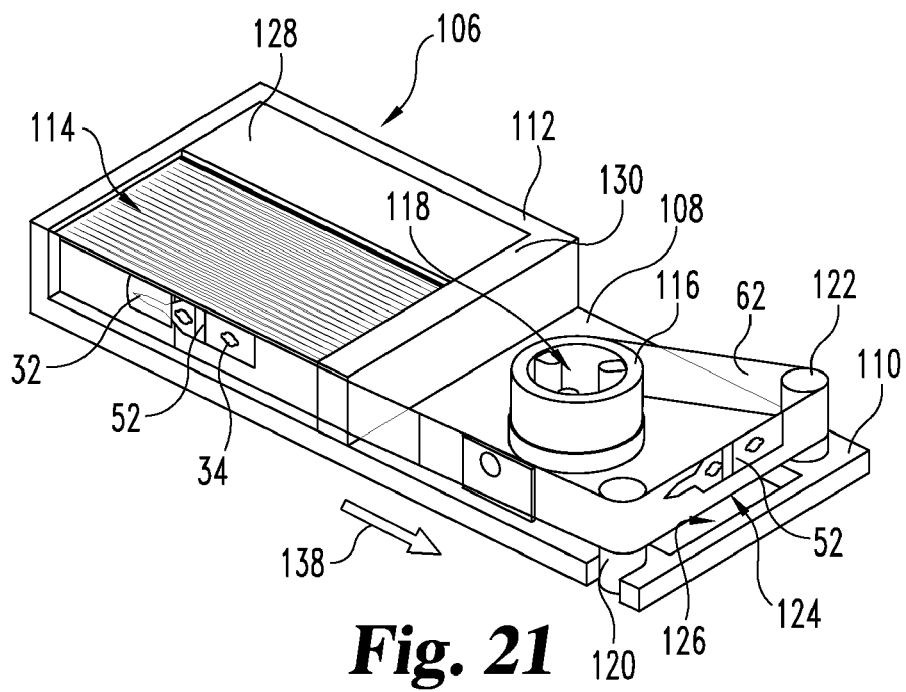
FIG. 21 is a perspective view of the FIG. 20 cassette with a portion of the housing removed.

A lancet-sampler cassette 106 according to one embodiment that is used to store and index the cassette tape 62 will now be described with reference to FIGS. 20 and 21. The cassette 106 includes a housing 108 that has opposing housing panels 110 and a storage wall 112 that defines a storage compartment 114 where an unused section of the tape 62 is stored. In FIGS. 20 and 21, a peripheral wall that wraps around the cassette 106 between the opposing panels 110 has been removed so that the inner workings of the cassette 106 can be easily viewed. It should be recognized that the cassette 106 can include one or more sections of the peripheral wall to protect and/or maintain the sterility of the tape 62.

A spool 116 extends between and is rotatably coupled to the opposing housing panels 110. The spool 116 is used to move the tape 62, and the tape 62, once used, is wrapped around spool 116. As can be seen, the spool 116 has a sprocket opening 118 that is configured to receive a sprocket that is used to rotate the spool 116. First 120 and second 122 guide pins or rollers for guiding the tape 62 in the cassette 106 are rotatably coupled to the housing 108. In the illustrated embodiment, the cassette 106 has two guide pins 120, 122, but the cassette 106 in other embodiments can include more or less guide pins than are shown, such as no guide pins. Looking at FIG. 21, the first 120 and second 122 pins are at one end of the cassette 106 and form a triangular pattern with the spool 116. It should be recognized that the pins 120, 122 and the spool 116 can be oriented in other manners. Between the first 120 and second 122 guide pins, the tape 62 has an acquisition section 124 where the fluid sample is acquired with the lancet-sampler 52 and analyzed. At the acquisition section 124, the opposing panels 110 of the housing 108 have one or more sensor openings 126 in which a sensor reader of the meter is received in order to read the test pads 64 on the tape 62. It is contemplated that in other embodiments the sensor openings 126 can be omitted when the sensor reader is located elsewhere along the cassette 106. Depending on the analysis technique used, the sensor reader can include an optical sensor or electrical contacts, for example.

Inside the storage compartment 114, the tape 62 is folded in a fanfold fashion. Looking at FIG. 21, the tape 62 is folded with blank sections between each lancet-sampler 52 so that the lancet-samplers 52 face in the same direction. In the illustrated embodiment, the lancet-samplers 52 are oriented in a tail first configuration in which the lancet tip 32 extends opposite to the direction the tape 62 travels during indexing. In other words, the tail or lancet body 34 of the lancet-sampler 52 is the leading end as the lancet-sampler 52 is moved. With this tail first orientation, the risk of the lancet 30 piercing the tape 62 is reduced when the lancet-sampler 52 is wrapped around the spool 116. Likewise, the risk of jamming the spool 116 is reduced when the tape 62 is wrapped around the spool 116 in a tail first orientation. Nevertheless, it is envisioned that in other embodiments the lancet-samplers 52 can be oriented in other manners, such as by having a head or lancing tip first orientation, and the tape 62 can be folded in other manners. For example, the tape 62 can omit the blank sections and have a lancet sampler on every fold. The storage compartment 114 can further include a desiccant 128 for reducing harmful humidity in the storage compartment 114. The storage wall 112 includes a divider wall section 130 that separates the storage compartment 114 from the portion of the cassette 106 that contains the spool 116. As will be explained below, the divider wall section 130 assists in pulling the protective cover from the lancet tip 32.

Figure 22A:
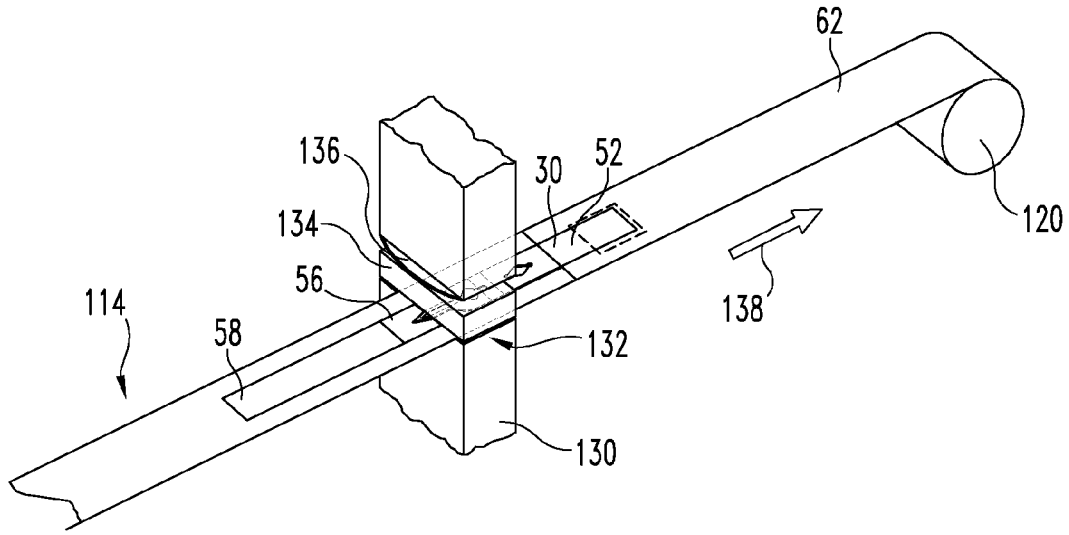
FIGS. 22A and 22B are perspective views of the carrier tape in the FIG. 20 cassette that illustrate a technique for removing the protective cover from the lancet-sampler.
Figure 22B:
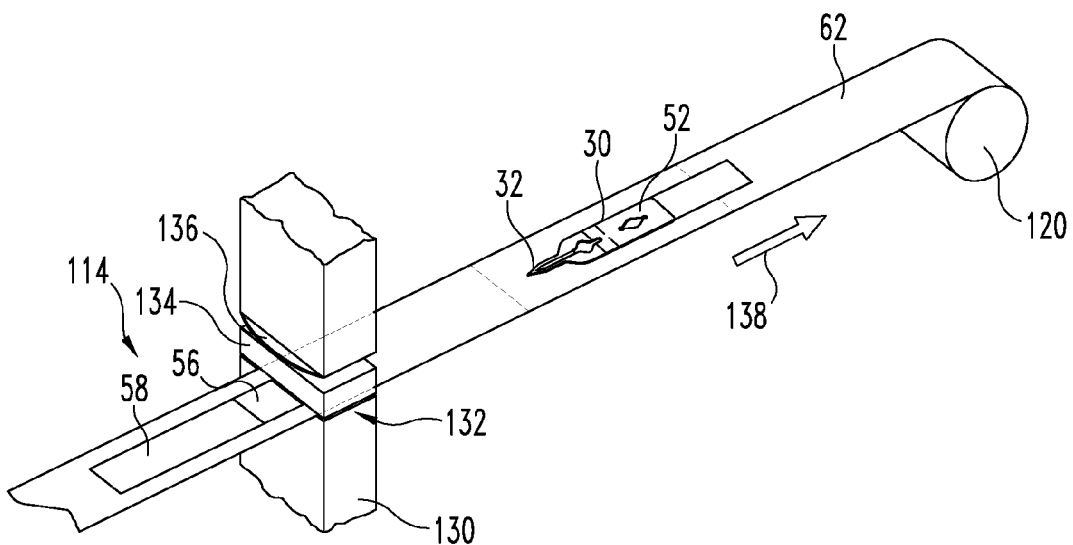

Turning to FIGS. 22A and 22B, the divider wall section 130 has a slot 132 through which the tape 62 passes. On one side of the slot 132, the divider wall section 130 has an engagement block or portion 134 that is biased towards the tape 62 by a spring 136. In one form, the engagement block 134 is made from resilient material such that the engagement block 134 can act like a seal so as to prevent contamination of the storage compartment 114. In the illustrated embodiment, the spring 136 is a leaf spring. However, it should be recognized that the spring 136 can include other types of springs, such as a coil spring, and/or other resilient means. For example, in another embodiment, the divider wall section 130 is made from springy material that substitutes for the spring 136. The gap height of the slot 132 is sized large enough so as to allow the tape 62 to pass through, but the gap height of the slot 132 is sized small enough such that the engagement block 134 is able to engage the protective cover 56 in order to pull the cover 56 from the lancet tip 32.

Looking at FIG. 22A, as the spool 116 indexes the tape in an indexing direction 138, the lancet-sampler 52 passes through the slot 132. Once the protective cover 56 reaches the engagement block 134, the cover 56 engages the engagement block 134 because the protective cover 56 is too thick to readily pass through the slot 132. As the spool 116 continues to pull on the tape 62 in the indexing direction 138, the protective cover 56 is pulled from the lancet tip 32 (FIG. 22B). Once the protective cover 56 is pulled from the lancet 30, the spool 116 keeps on pulling the tape 62 with sufficient force so that the engagement block 134 deflects and/or deforms to allow the protective cover 56 to pass through the slot 132. Afterwards, the lancet-sampler 52 is positioned at the acquisition section 124 of the cassette 106, as is depicted in FIG. 21. The spool 116 slackens the tape 62, which in turn allows the lancet 30 to be fired to cut the incision. After lancing, the spool 116 takes up the slack, and the lancet 30 is disposed over the test pad 64 such that the collected fluid sample is deposited on the test pad 64. Via the sensor openings 126, the meter is able to analyze the sample on the test pad 64. Once the test is completed, the spool 116 rotates to wrap the now used lancet-sampler 52 around the spool 116. With the tail first orientation of the lancet 30 on the tape 62, the risk of the lancet tip 32 cutting and/or breaking the tape 62 is reduced. Subsequently, the unused lancet-samplers 52 in the storage compartment 114 are indexed in a similar fashion.

Figure 23:
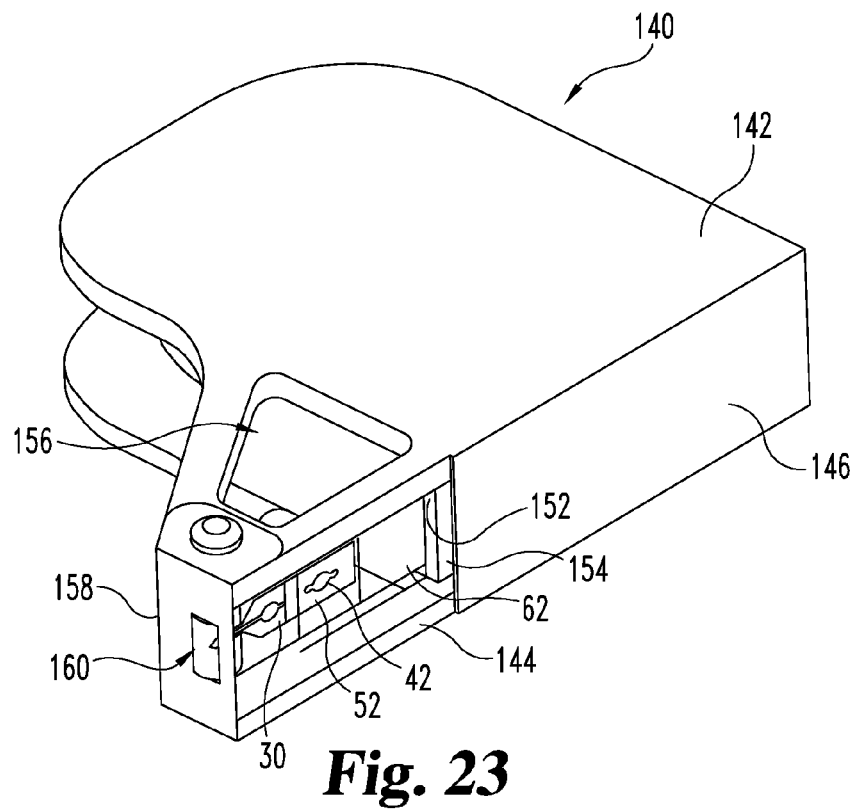
FIG. 23 is a perspective view of a cassette according to another embodiment that houses the carrier tape.
Figure 24A:
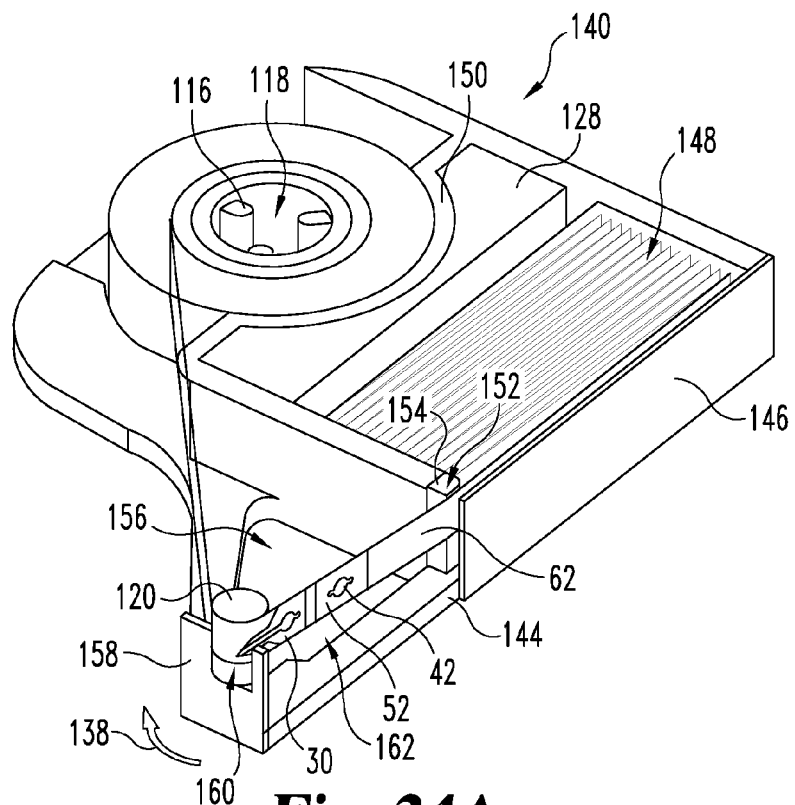
FIGS. 24A, 24B, and 24C are perspective views of the FIG. 23 cassette with a portion of its cassette housing removed that illustrate a technique for flipping a lancet to a tail first orientation.

A lancet-sampler cassette or cartridge 140 according to still yet another embodiment will be initially discussed with reference to FIG. 23. The cassette 140 includes a housing 142 with opposing housing walls 144 and a peripheral wall 146 that defines a storage compartment 148 for storing an unused section of the tape 62 in a fan folded fashion, as is depicted in FIG. 24A. Like the previously described embodiment, the cassette 140 has the spool 116 for moving the tape 62 as well as the guide pin 120 for guiding the tape 62 in the cassette 140. Near the spool 116, the storage compartment 148 has a curved wall section 150 that coincides with the shape to the tape 62 when wrapped around the spool 116. Desiccant 128 is disposed inside the storage compartment 148 so as to reduce humidity inside the storage compartment 148. As can be seen, the storage compartment 148 has an exit opening 152 where the tape 62 exits the storage compartment 148. At the exit opening 152, the cassette 140 has a seal 154 to maintain the humidity levels within the storage compartment 148 as well as reduce the chance of contamination in the storage compartment 148. The housing 142 further has one or more sensor openings 156 in which a sensor reader of the meter is received in order to read the test pads 64 on the tape 62.

Looking at FIG. 24A, the exit opening 152, the guide pin 120, and the spool 116 are oriented in a triangular relationship with one another such that the tape extends at an acute angle in relation to the guide pin 120. At the guide pin 120, the cassette 140 has an end or flip wall member 158 that defines a lancet opening 160 through which the lancets 30 extend during lancing. As shown, the lancet opening 160 is aligned with the guide pin 120. Between the end wall 158 and the exit opening 152, the cassette 140 has an actuation opening 162 where the firing or actuation mechanism of the meter engages the lancet 30 of the lancet-sampler 52.

In the illustrated embodiment, the lancet-samplers 52 are aligned on the tape 62 in a face or lancet tip first orientation in which the lancet tip 32 of the lancet 30 extends towards the spool 116 on the tape 62. With the tip first orientation of the lancets 30, removal of the protective cover 56 from the lancet tip 32 is simplified, and likewise, actuation of the lancet 30 is simplified. However, as mentioned before, the tip first orientation can create complications when the tape 62 is wrapped around the spool 116. For instance, the lancets 30 can cut or even break the tape 62, and the spool 116 can become jammed with the lancets 30. To address these concerns, the cassette in FIG. 24A stores and dispenses the lancet-samplers 52 in a tip first orientation, and then flips the lancets 30 on the tape 62 to a tail first orientation before the used section of tape 62 is wrapped around the spool 116.

Figure 24B:
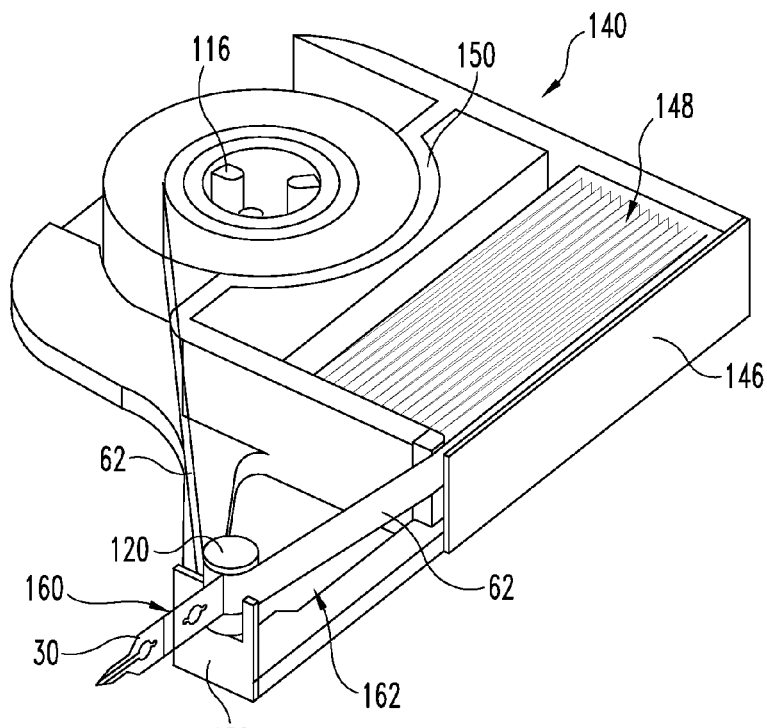
Figure 24C:
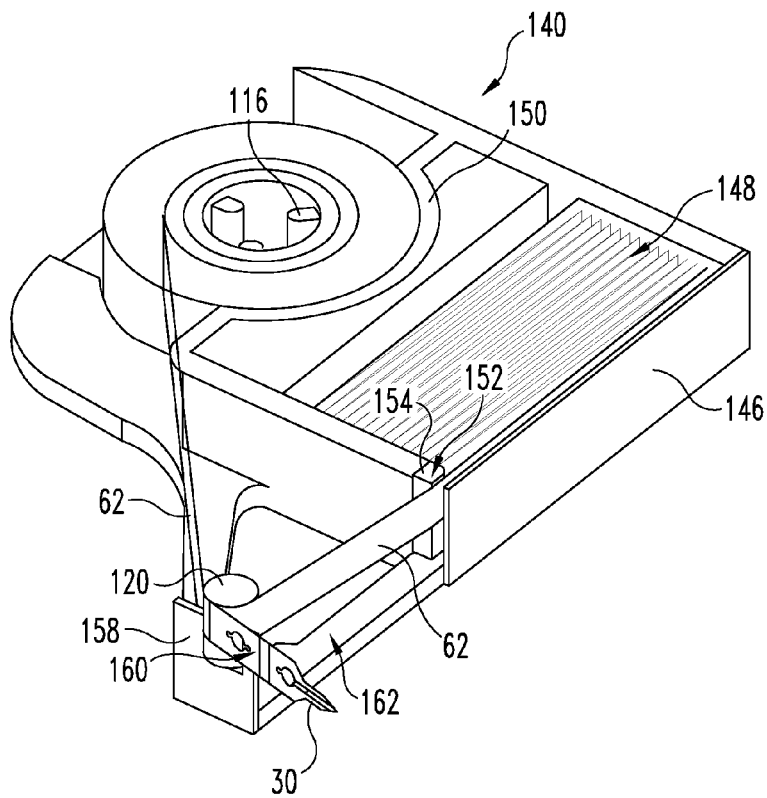

In one embodiment, after the lancet-sampler 52 exits the storage compartment 148, the firing mechanism engages the actuator engagement hole 42 in the lancet 30 in order to hold the lancet 30 in place. The meter and/or the cassette 140 includes a clutch that allows the tape 62 to be only moved in the indexing direction 138. The firing mechanism is then used to pull the lancet 30 in an opposite direction to the indexing direction, thereby pulling the protective cover 56 from the lancet 30. It should be recognized that the protective cover 56 can be removed in other manners. For example, as the firing mechanism holds the lancet 30 in another embodiment, the spool 116 rotates so as to pull the protective cover 56 from the lancet 30. Once the protective cover 56 is removed, as is depicted in FIG. 24A, the lancet 30 is fired, and the fluid sample is collected with the lancet-sampler 52 for analysis. Once the lancet-sampler 52 is used, the spool 116 indexes the tape 62. Looking at FIG. 24B, as the tape 62 is indexed, the lancet 30 extends from the tape 62 because the tape 62 bends acutely around the guide pin 120. Referring to FIG. 24C, as the spool 116 continues to index the tape 62, the lancet 30 hits the wall of the lancet opening 160 in the flip member 158, which in turn causes the lancet 30 to face in a tail first orientation. With the lancet 30 flipped in a tail first orientation, the lancet 30 and tape 62 can be safely wrapped around the spool 116 as the spool 116 rotates. It should be appreciated that in other embodiments lancing, fluid sampling, and/or analysis can occur after the lancet 30 is flipped. For example, in one embodiment, the lancet 30 lances the tissue as the lancet 30 is flipped (FIG. 24B), and the fluid sample is then analyzed with the lancet 30 in a tail first orientation.

Figure 25:
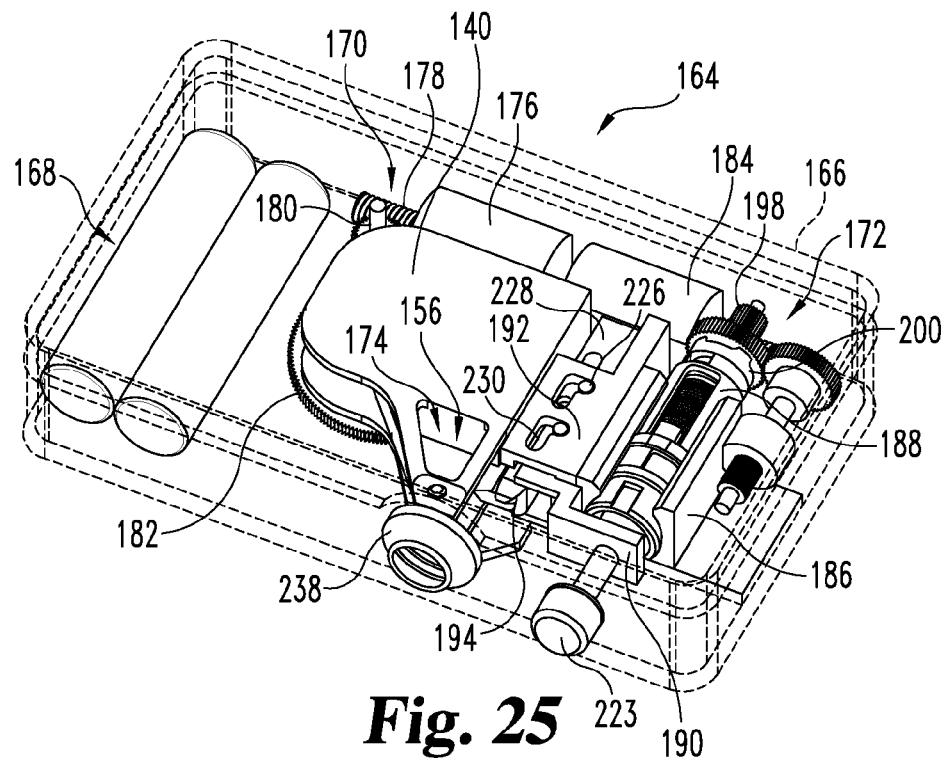
FIG. 25 is a front perspective view of a meter in which the FIG. 23 cassette can be loaded.
Figure 26:
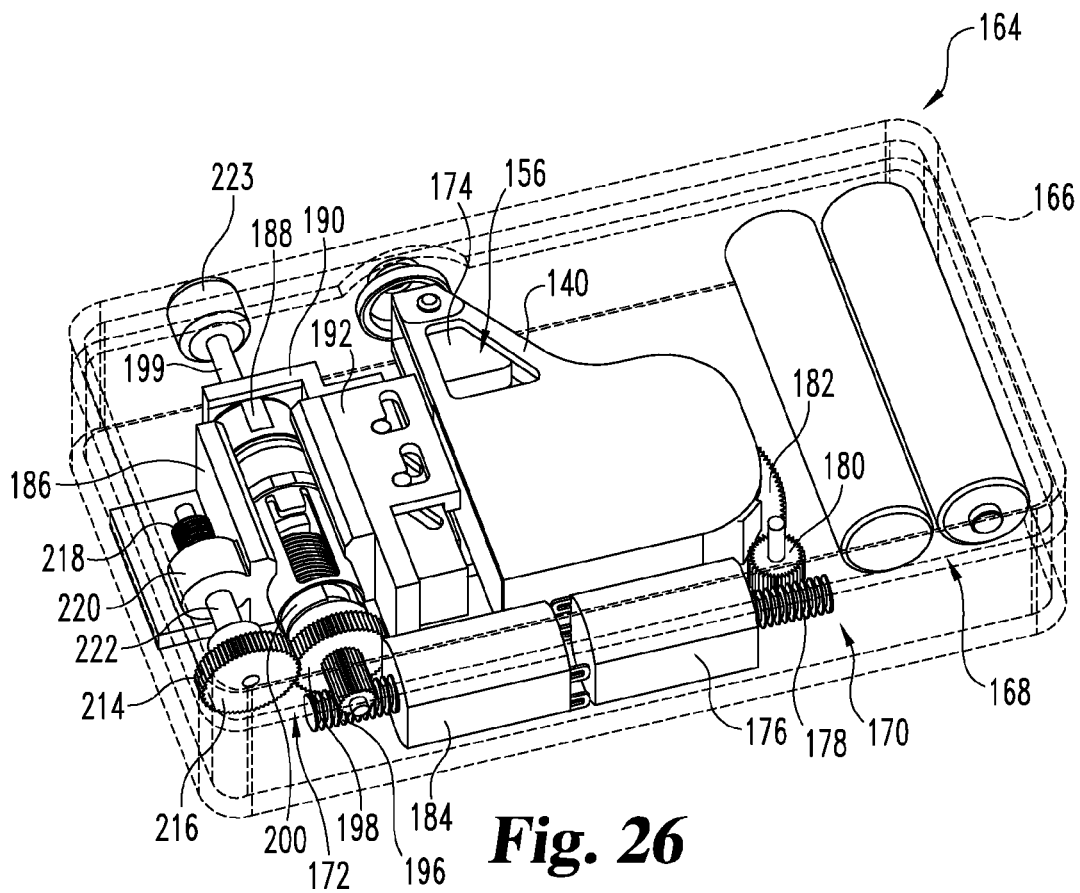
FIG. 26 is a rear perspective view of the FIG. 25 meter.

A meter 164 into which the cassette 140 can be loaded is illustrated in FIGS. 25 and 26. In FIGS. 25 and 26, various electrical systems, such as circuit boards and wires, as well as other components have been removed so that the main systems of the meter 164 can be easily viewed. In the illustrated embodiment, the meter 164 includes a housing 166 in which other components of the meter 164 are housed. The meter 164 further includes a power supply 168, an indexing mechanism 170 configured to index the cassette 140, a firing mechanism 172 configured to fire the lancets 30, and a sensor system 174 configured to analyze the collected fluid samples. The housing 166, which is shown in phantom lines in FIGS. 25 and 26, has a rectangular shape, but the housing 166 can be shaped differently in other embodiments. The power supply 168 is used to power the various systems in the meter 164, like the indexing mechanism 170, the firing mechanism 172, and the sensor system 174. The power supply 168 in the depicted embodiment includes batteries, but it should be appreciated that other types of power sources can be used, such for example electrical outlets or fuel cells. As shown, the sensor system 174 is received inside the sensor opening 156 of the cassette 140. In the depicted embodiment, the sensor system 174 includes an optical sensor, but it should be recognized that the sensor system 174 can be configured to analyze fluid samples in other manners, such as through electrochemical analysis. When fluid is analyzed electrochemically, the sensor system 174 can for example include contacts configured to electrically couple to the contacts 104 of the electrochemical version of the lancet-sampler 100 and/or can include a transceiver that wirelessly communicates with the lancet-sampler 100.

The indexing mechanism 170 in the meter 164 includes an indexing motor 176, which in the illustrated example is a reversible electric motor with a drive worm 178. The indexing motor 176 is powered by the power supply 168. It again should be appreciated that other types of motors can be used. The drive worm 178 rotates an intermediate gear 180, which in turn rotates a main drive gear 182. The main drive gear 182 includes a sprocket that is received in the sprocket opening 118 of the spool 116. As the indexing motor 176 rotates the drive worm gear 178, the intermediate gear 180 and the main drive gear 182 rotate, which in turn rotates the spool 116, thereby indexing the tape 62. It is contemplated that the indexing mechanism 170 can be configured differently in other embodiments.

With reference to FIGS. 25, and 26, the firing mechanism 172 includes a firing or drive motor 184, a carriage 186, a lancing or actuator unit 188 carried on the carriage 186, a transmission member 190 for transmitting force from the lancing unit 188, a guide 192 that is secured to the housing 166, and an actuator arm or member 194 that is configured to actuate the lancet 30. The drive motor 184 in the illustrated embodiment is a reversible electric motor 184, but in other embodiments, the drive motor 184 can include other types of motors, like a pneumatic motor and/or a nonreversible motor. When the drive motor 184 is only able to supply output in one direction (i.e., a nonreversible motor), the firing mechanism 172 can incorporate a transmission that is able to change the output. The drive motor 184 has a worm gear 196 that engages an intermediate, priming gear 198 that is configured to prime or cock the lancing unit 188. As shown, the priming gear 198 is rotatably coupled to a guide shaft or rod 199 that is coupled to the housing 166 at both ends.

Looking at FIG. 26, the lancing unit 188 is slidably coupled to the guide shaft 199. In the illustrated embodiment, the lancing unit 188 is mechanically driven, and in particular, the lancing unit 188 includes a torsion barrel type firing mechanism, like an ACCU-CHEK® SOFTCLIX or MULTICLIX brand device driver (Roche Diagnostics, Indianapolis, Ind.). For detailed examples of some types of lancing units 188, please refer to U.S. Pat. Nos. Re. 35,803 to Lange et al. and U.S. Pat. No. 6,419,661 to Kuhr et al., which are hereby incorporated by reference in their entirety. It should be recognized that other types of firing mechanisms can be used as well. By way of non-limiting examples, the lancing unit 188 in other embodiments can include other types of mechanical drivers, electromechanical type drivers, electrical type drivers, pneumatic drivers, or some combination thereof.

Figure 27A:
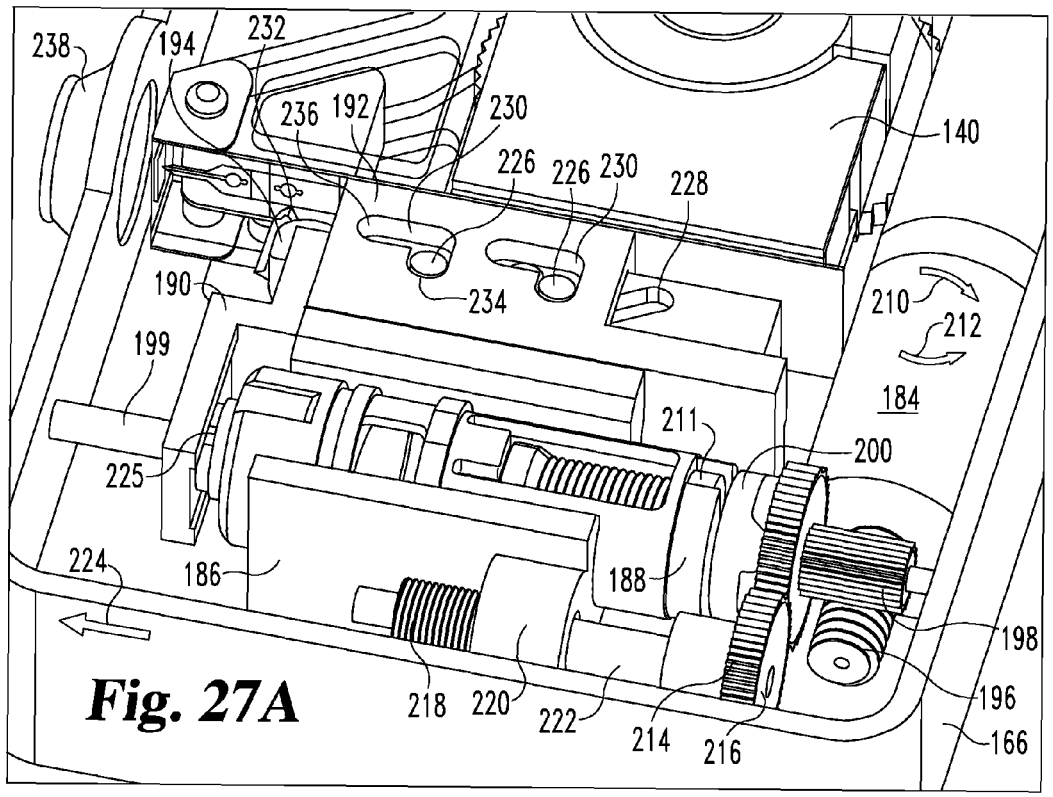
FIG. 27A is an enlarged perspective view of FIG. 25 meter.
Figure 27B:
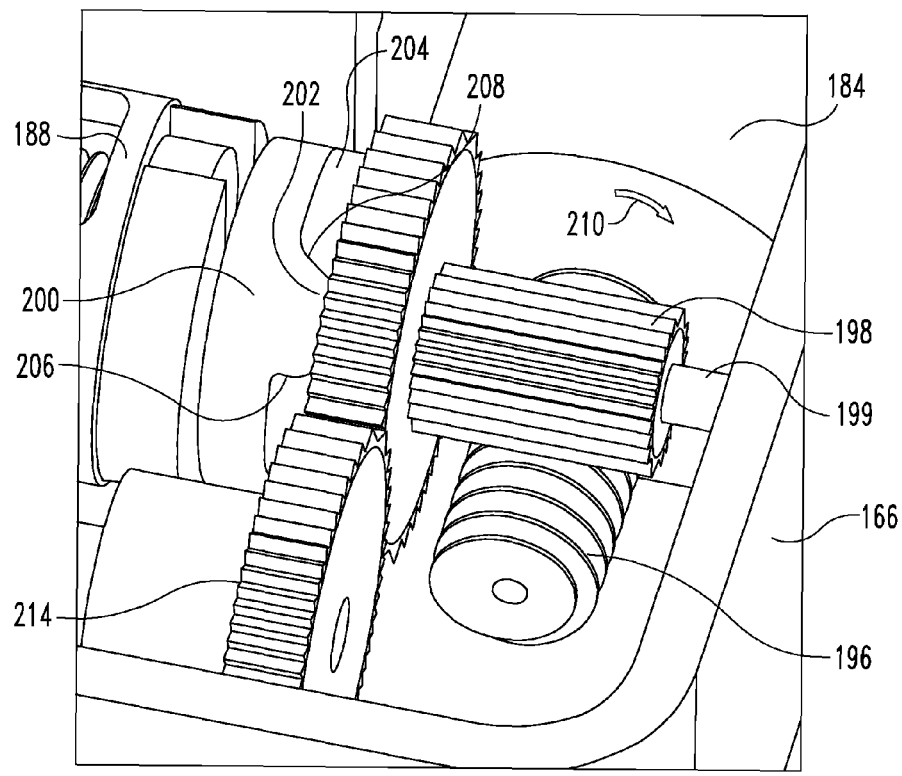
FIG. 27B is an enlarged view of a clutch of a lancing unit engaged with a priming gear in the FIG. 25 meter.
Figure 27C:
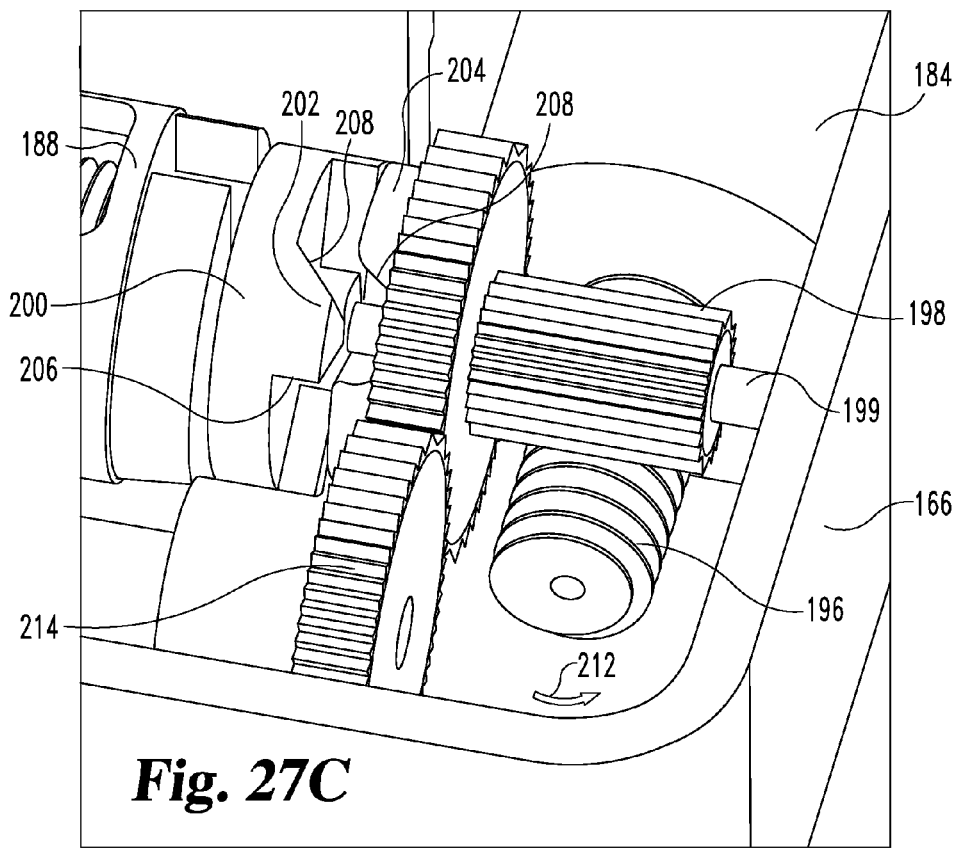
FIG. 27C is an enlarged view of the clutch disengaged from the priming gear in the FIG. 25 meter.

Facing the priming gear 198, the lancing unit 188 has a clutch 200 that is configured to engage the priming gear 198, as is depicted in FIG. 27A. The clutch 200 is only able to rotate in one direction so as to prime the lancing unit 188. FIG. 27B shows an enlarged view of the priming gear 198 and clutch 200 when engaged. As can be seen, the clutch 200 has clutch fingers 202 that engage with clutch teeth 204 on the priming gear 198. The clutch fingers 202 on the clutch 200 are generally resilient and extend in a radial inwards direction, towards the guide shaft 199. Turning to FIGS. 27A and 27B, both the clutch fingers 202 and clutch teeth 204 have corresponding engagement surfaces 206 that extend in a general orthogonal direction and disengagement surfaces 208 that are acutely angled. As the drive motor 184 rotates the priming gear 198 in a clockwise direction 210 (FIG. 27B), the engagement surfaces 206 of the priming gear 198 and the clutch 200 engage such that the priming gear 198 rotates the clutch 200. As the clutch 200 is likewise rotated in the clockwise direction 210, the lancing unit 188 is primed by winding of the spring inside the lancing unit 188. Inside the lancing unit 188, the clutch has a second set of one or more fingers 211 (FIG. 27A) that engage notches in the lancing unit 188 so that the clutch 200 is only able to rotate in a direction that winds the spring inside the lancing unit 188 such that the lancing unit 188 is primed. Referring to FIG. 27C, when the drive motor 184 rotates the priming gear 198 in a counterclockwise direction 212, due the resilient nature of the clutch fingers 202, the disengagement surfaces 208 generally slide across one another such that the priming gear 198 does not rotate the clutch 200. Although the clutch 200 is disengaged from the priming gear 198, the second set of fingers 211 of the clutch 200 inside the lancing unit 188 prevent the spring inside the lancing unit 188 from unwinding, thereby leaving the lancing unit 188 in a primed state.

Returning to FIGS. 26 and 27A, the carriage 186, which holds the lancing unit 188, is operatively coupled to the priming gear 198 through a carriage actuation member or screw 214. At one end, the carriage actuation screw 214 includes a gear head 216 that engages the priming gear 198. Opposite gear head 216, the carriage actuation screw 214 has a threaded end 218 that is configured to threadedly engage an internally threaded collar 220 on the carriage 186. Between the gear head 216 and the threaded end 218, the carriage actuation screw 214 has an unthreaded section 222. During priming of the lancing unit 188, the threaded collar 220 of the carriage 186 is positioned along the unthreaded section 222 of the carriage actuation screw 214. As the drive motor 184 rotates the priming gear 198 in the clockwise direction 210 to prime the lancing unit 188, the carriage actuation screw 214 rotates in a counterclockwise direction 212. With the carriage actuation screw 214 rotating in a counterclockwise direction 212, the threaded collar 220 remains over the unthreaded section 222 and disengaged from the threaded end 218. While the threaded collar 220 of the carriage 186 remains disengaged from the threaded end 218, the carriage 186 remains stationary.

At the end of the shaft 199 in FIG. 26, the meter 164 includes an optional button 223. In one embodiment, the button 223 is adjustable relative to the shaft 199 so as to be able to adjust the penetration depth of the lancet 30. In another embodiment, the button 223 is used to fire the lancet 30. Specifically, the button 223 in one embodiment includes a hollow tube that is slidably disposed around the shaft 199 and extend to the lancing unit 188. When the button 223 is pushed, the hollow tube releases the spring inside the lancing unit 188 such that an extension shaft 225 extends from the lancing unit 188. In further embodiments, the hollow tube of the button 223 is not disposed around the shaft 199, but rather, the hollow tube acts as a section of the shaft 199. It should be appreciated that firing can be initiated manually by pressing the button 223, automatically, or in some other manner. Again, the button 223 can be optional in other embodiments, and the button 223 can be also located at places other than is shown in the drawings. Moreover, the lancing unit 188 can be fired in other manners.

After the lancing unit 188 is primed and lancing is initiated by pressing the button 223 or in some other manner, the drive motor 184 in one embodiment is reversed, and the priming gear 198 is rotated in the counterclockwise direction 212. In another embodiment, the firing mechanism 172 does not require the button 223 or some other input device to be pushed in order to reverse the output of the drive motor 184. For example, after the priming gear 198 is rotated a predetermined number of times, the drive motor 184 is reversed. Upon reversal of the drive motor 184, the carriage actuation screw 214 rotates in the clockwise direction 210, and consequently, the threaded collar 220 of the carriage 186 engages the threaded end 218 of the carriage actuation screw 214. As the carriage actuation screw 214 continues to rotate in the clockwise direction 210, the threaded end 218 causes the carriage 186 along with the lancing unit 188 to move away from the priming gear 198 in an extension direction, as is indicated with arrow 224 in FIG. 27A. Eventually, as the carriage 186 continues to move the lancing unit 188 in direction 224, the clutch 200 on the lancing unit 188 disengages from the priming gear 198 (FIG. 27C).

Figure 28:
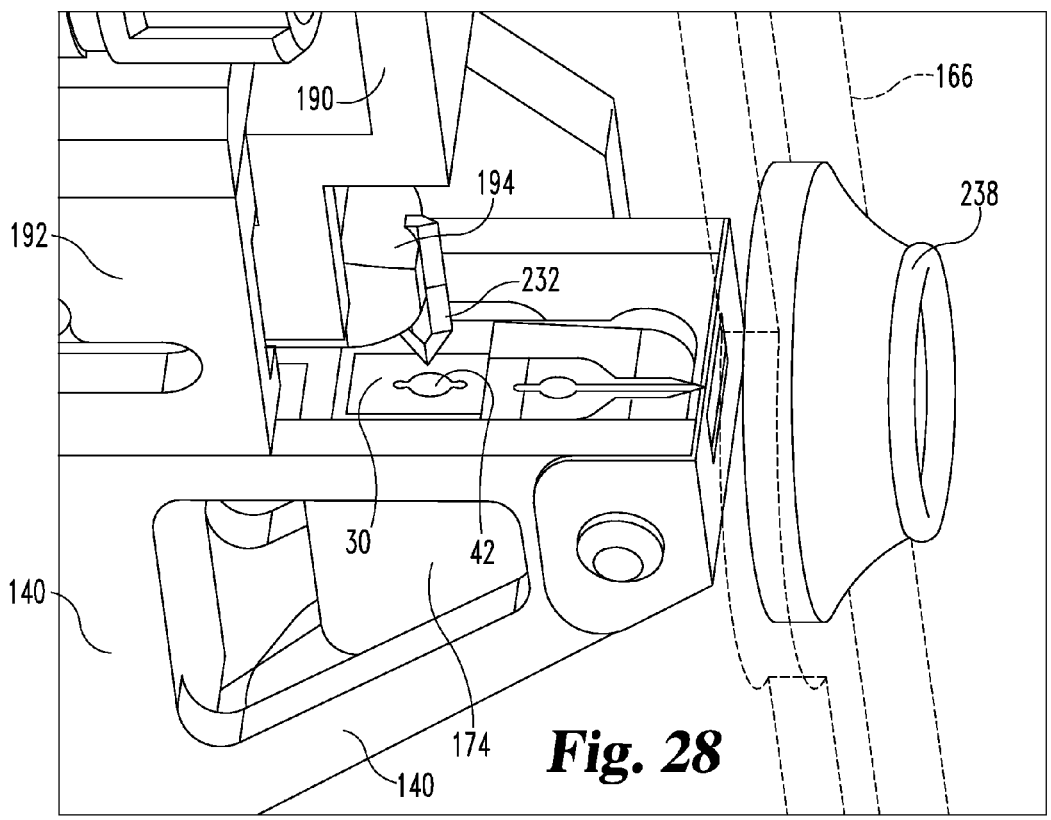
FIG. 28 is an enlarged view of a portion of the FIG. 25 meter where the lancet is fired from the meter.

Opposite the clutch 200, as is shown in FIG. 27A, the lancing unit 188 is coupled to the transmission member 190 that transmits the movement of the carriage 186 as well as the firing motion from the extension shaft 225 of the lancing unit 188 to the actuator member 194. Returning to FIG. 25, the transmission member 190 is received inside the guide member 192, and the actuator member 194 is similarly received inside the transmission member 190. Looking at FIG. 27A, the actuator member 194 in the illustrated embodiment has a pair of guide pins 226 that extend from opposing sides of the actuator member 194, but it should be recognized that the actuator member 194 can have more or less guide pins 226. The guide pins 226 extend through corresponding transmission slots 228 in the actuator member 194 and into guide slots 230 in the guide member 192. The guide member 192 is fixed to the housing 166 such that the guide member 192 does not move relative to the housing 166. Referring to FIGS. 27A and 28, the actuator member 194 has an engagement blade 232 that is configured to engage the keyhole 42 in the lancet 30.

As shown in FIG. 27A, the guide slots 230 in the guide member 192 are generally L-shaped, and the transmission slots 228 in the actuator member 194 are slanted or angled. The L-shaped guide slots 230 have first 234 and second 236 sections that extend orthogonally to one another. Depending on the desired travel path for the actuator member 194, the slots 228, 230 can be shaped differently in other embodiments. When the transmission member 190 slides relative to the guide member 192, such as during firing of the lancing unit 188 and/or when the carriage 186 is moved, the transmission slots 228 cause the guide pins 226 to move along the L-shaped path of the guide slots 230. When the guide pins 226 of the actuator member 194 move in the first sections 234 of the L-shaped guide slots 230, the engagement blade 232 of the actuator member 194 moves into engagement with the keyhole 42 of the lancet 30. Once the guide pins 226 reach the corners of the L-shaped guide slots 230, the transmission slots 228 in the moving transmission member 190 push the guide pins 226 in direction 224 along the second section 236 of the L-shaped guide slot 230. This in turn causes the lancet 30 to extend from a lancing cap 238 of the meter 164 in order to lance the tissue and/or collect fluid from the incision.

Figure 29A:
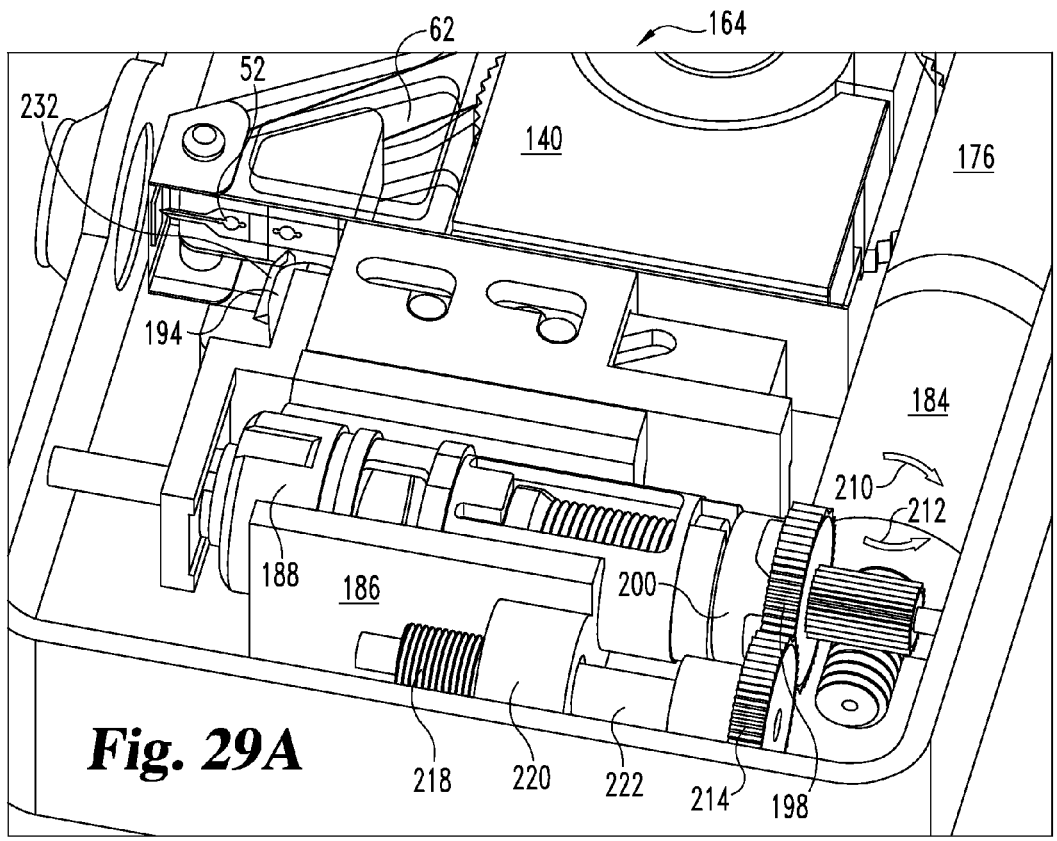
FIGS. 29A, 29B, 29C, 29D, 29E, and 29F are perspective views of the FIG. 25 meter during lancing and sampling.

A technique for obtaining and analyzing a fluid sample with the cassette 140 and meter 164 will be initially described with reference to FIG. 29A. To prime the lancing unit 188, the drive motor 184 rotates the priming gear 198 in the clockwise direction 210, which in turn rotates the clutch 200 of the lancing unit 188. During priming of the lancing unit 188, the carriage 186 holding the lancing unit 188 remains stationary because the carriage actuation screw 214 rotates in the counterclockwise direction 212 such that threaded collar 220 of the carriage 186 remains over the unthreaded section 222, disengaged from the threaded end 218 of the screw 214. As mentioned before, the indexing motor 176 is used to index the tape 62 in the cassette 140 so that the lancet-sampler 52 is properly positioned to engage the engagement blade 232 of the actuator member 194. In one example, the indexing motor 176 indexes the tape 62 after the lancing unit 188 is primed, but it should be recognized that the tape 62 can be indexed before, during, or after the lancing unit 188 is primed. During indexing of the tape 62, the protective cover 56 over the lancet tip 32 of the lancet 30 can be removed in a similar fashion as was described above with reference to the cassette 140. The firing mechanism 172 can be primed before or after the lancing cap 238 is placed against the skin or other tissue.

Figure 29B:
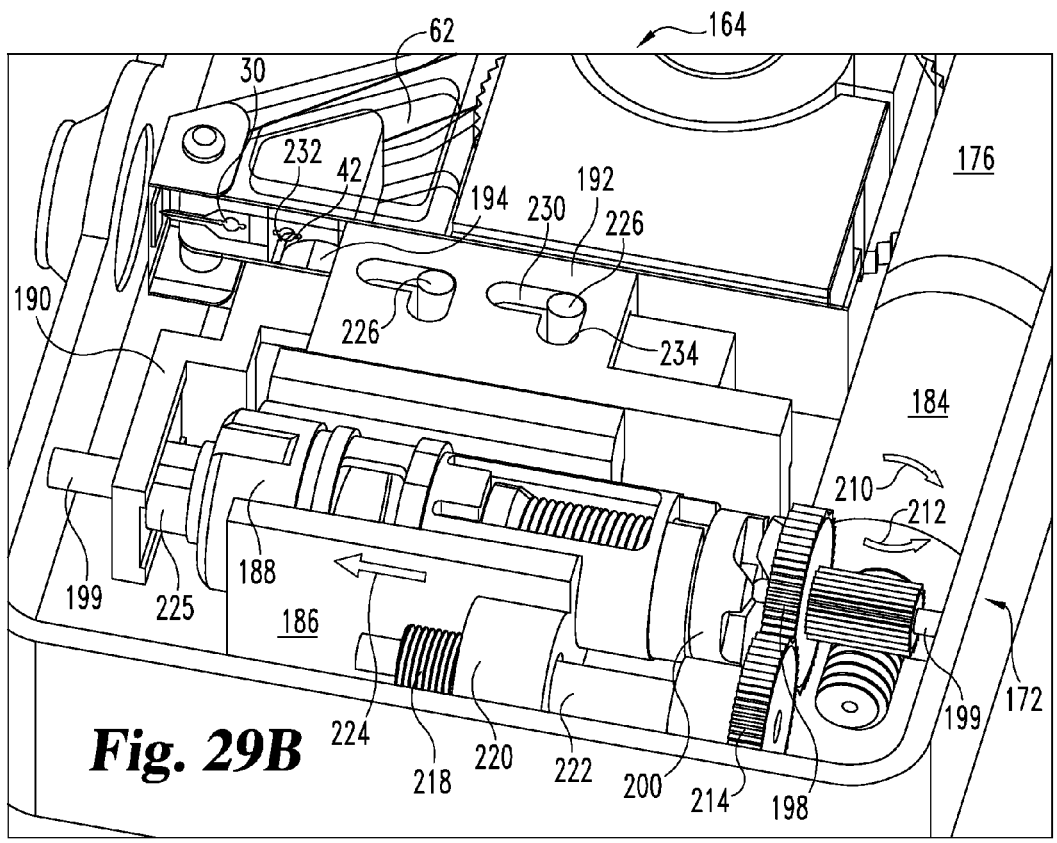

Turning to FIG. 29B, once the clutch 200 is rotated sufficiently to prime the lancing unit 188, the firing mechanism 172 is able to be fired. Firing can be initiated manually by the user, such as by pressing the button 223 (FIG. 26) or automatically by the meter 164. In one embodiment, firing of the lancing unit 188 is initiated after the actuator blade 232 engages the lancet 30, and in another embodiment, firing of the lancing unit 188 occurs before the actuator blade 232 engages the lancet 30. Upon priming the lancing unit 188, the driving motor 184 reverses such that the priming gear 198 rotates in the counterclockwise direction 212. As a result, the carriage actuation screw 214 rotates in the clockwise direction 210, which in turn causes the threaded collar 220 of the carriage 186 to engage the threaded end 218 of the screw 214. Once the collar 220 engages the threaded end 218, the carriage 186 moves away from the priming gear 198, as is indicated by direction arrow 224. Consequently, the lancing unit 188 along with the carriage 186 slides along the guide shaft 199, and the clutch 200 of the lancing unit 188 disengages from the priming gear 198. Although the clutch 200 is disengaged from the priming gear 198, the lancing unit 188 remains primed because the second set of fingers 211 (FIG. 27A) only allow the clutch 200 to be rotated in a priming direction, thereby preventing unwinding of the torsion spring inside the lancing unit 188. With the carriage 186 moving in direction 224, the transmission member 190 likewise moves in the same direction. In one embodiment, the lancing unit 188 does not fire when the carriage 186 is moved such that the movement of the carriage 186 is the sole source for moving the transmission member 190. In an alternative embodiment where the lancing unit 188 is fired at the same time the carriage 186 is moved, both the motion of the carriage 186 and the extension of the extension shaft 225 move the transmission member 190. The movement of the transmission member 190 as well as its transmission slots 228 in direction 224 cause the guide pins 226 to move along the first section 234 of the L-shaped guide slots 230. This in turn pushes the actuator blade 232 of the actuation member 194 into the keyhole 42 of the lancet 30, thereby engaging the lancet 30 to the firing mechanism 172. If the keyhole 42 is covered with a protective covering or film, the actuator blade 232 can be configured to puncture the film as well.

Figure 29C:
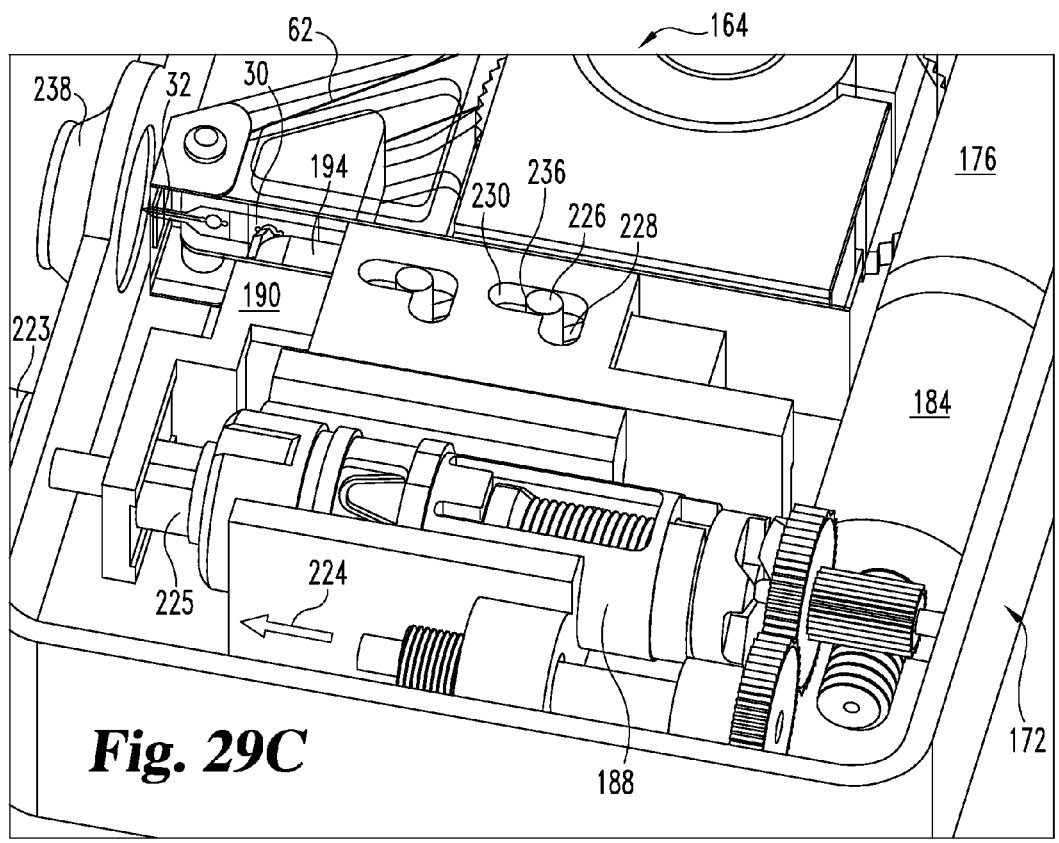

With reference to FIG. 29C, after the actuator blade 232 of the firing mechanism 172 engages the lancet, the drive motor 184 stops driving the carriage 186 in direction 224. At this point, the firing mechanism 172 is prepared to fire the lancet 30. Once prepared, the lancing unit 188 is fired so that the extension shaft 225 extends from the lancing unit 188 in direction 224. As noted above, the lancing unit 188 can be automatically fired by the meter 164 or manually fired by pressing the button 223 and/or by having the user interface with some other type of input device. As mentioned above, the lancing unit 188 in other embodiments can be fired at the same time the carriage 186 is moved in direction 224. Returning to the illustrated embodiment, after the firing mechanism 172 engages the lancet 30 and the user presses the button 223, the lancing unit 188 extends the extension shaft 225. As the extension shaft 225 moves, the transmission slots 228 in the moving transmission member 190 cause the guide pins 226 of the actuator arm 194 to slide in the second section 236 of the guide slot 230. Consequently, the actuator arm 194 extends or fires the lancet 30 such that the lancet tip 32 cuts an incision in the tissue.

Figure 29D:
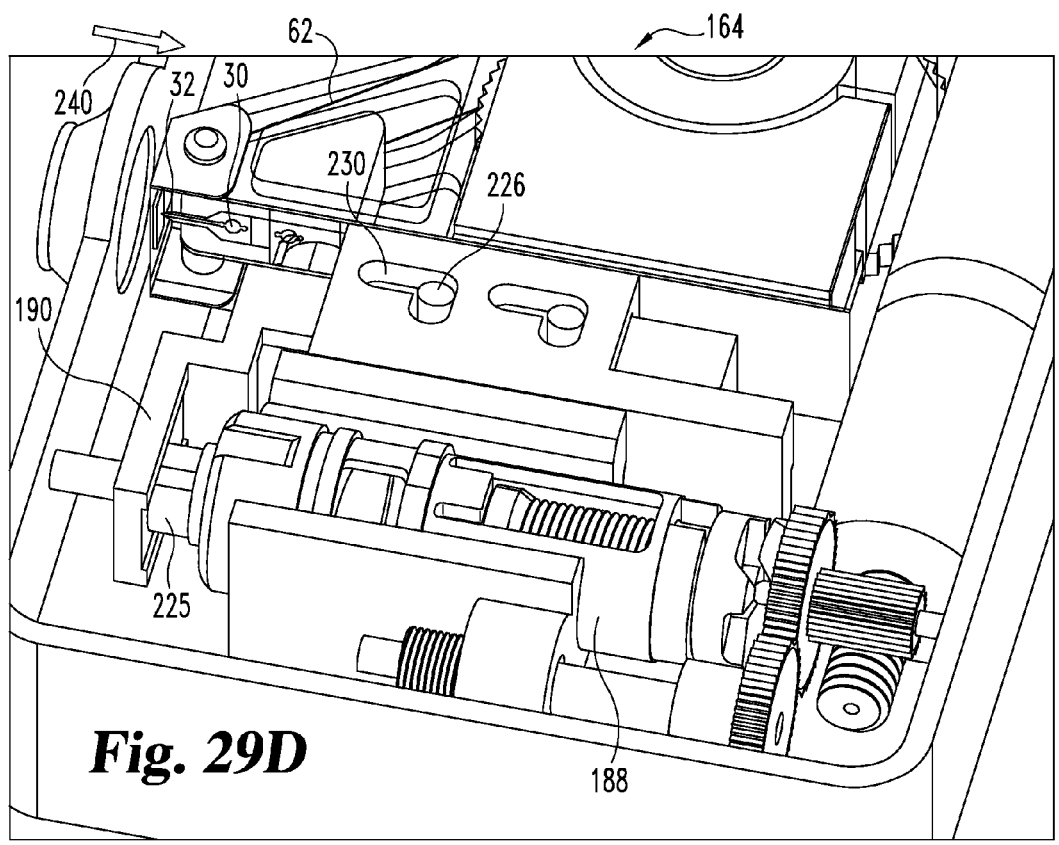
Figure 29E:
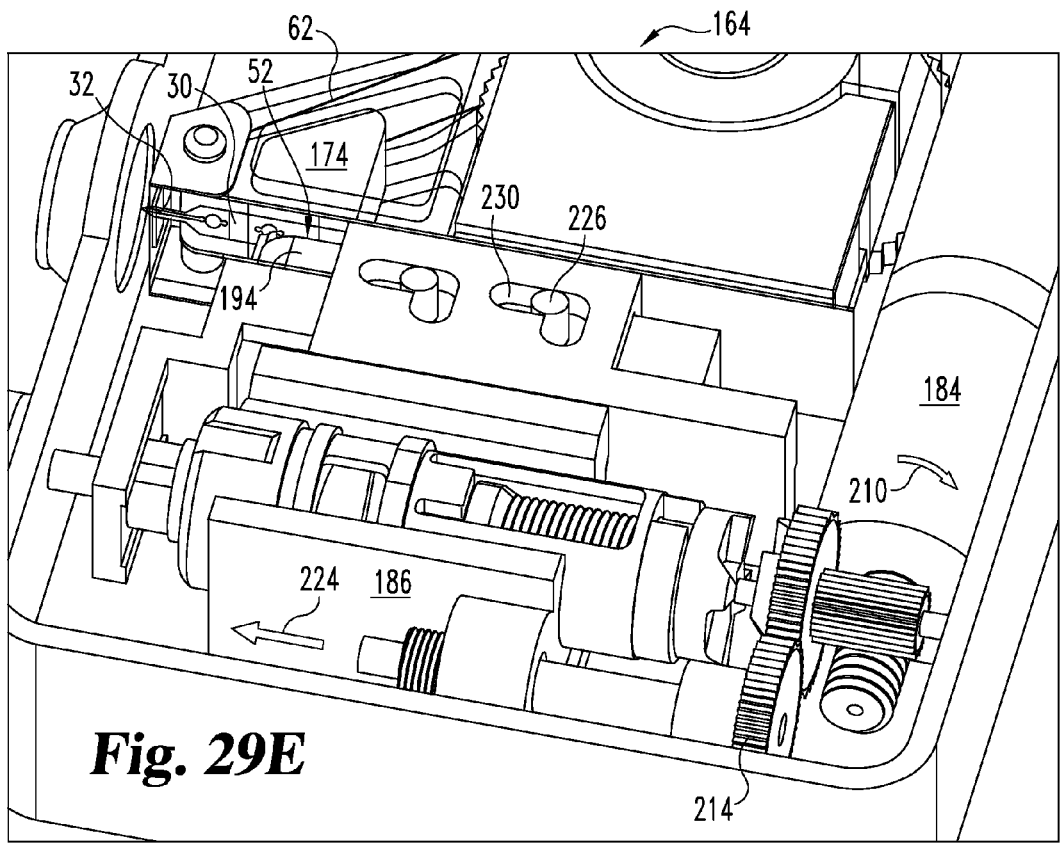

After cutting the incision, the lancing unit 188 is configured to retract the extension shaft 225 in a retraction direction, as is indicated by arrow 240 in FIG. 29D. This in turn causes the guide pins 226 to move in the retraction direction 240, which results in the lancet 30 retracting from the incision. Removing the lancet 30 from the incision tends to reduce pain as well as potentially enhance bleeding from the incision because the lancet tip 32 does not plug the incision. Afterwards, the lancet 30 can be reapplied so that the lancet tip 32 is dipped into the drop of body fluid on the tissue such that a fluid sample is drawn into the lancet-sampler 52. Looking a FIG. 29E, in order to reapply the lancet tip 32 to the drop of fluid, the drive motor 184 rotates the carriage actuation screw 214 in the clockwise direction 210, thereby moving the carriage 186 in the extension direction 224. As the carriage 186 moves, the actuator arm 194 along with the lancet 30 move in direction 224, towards the incision.

Figure 29F:
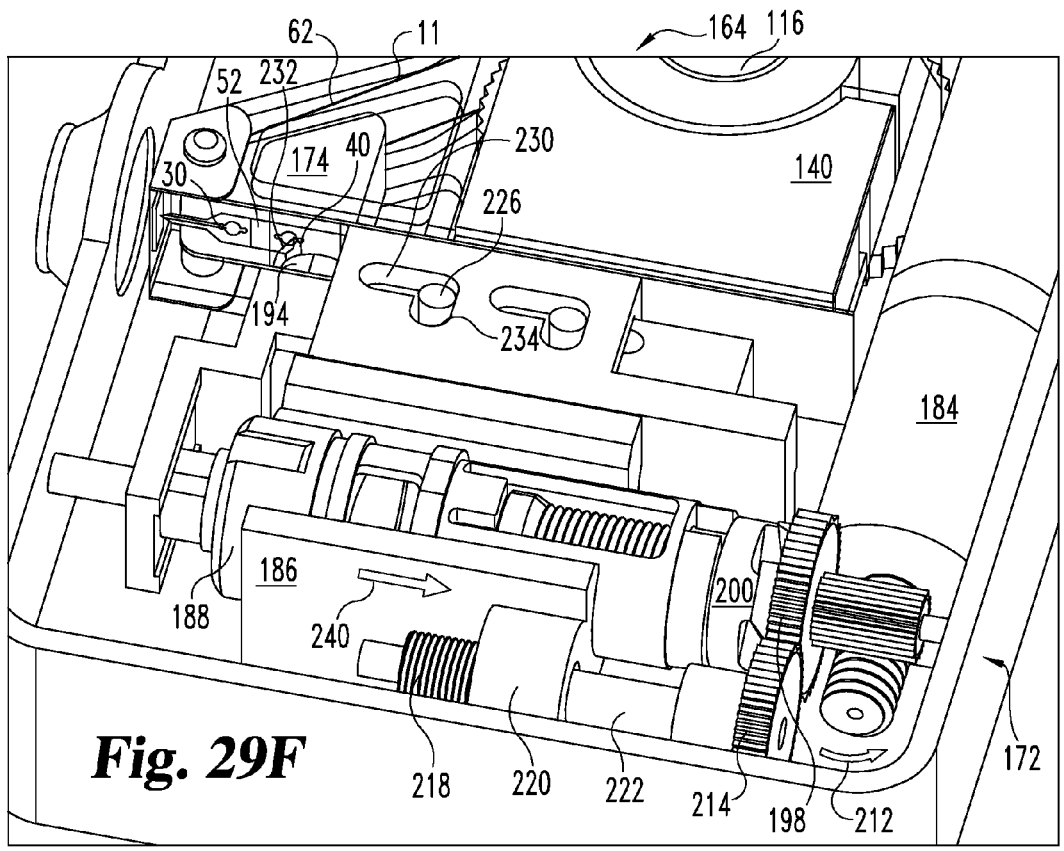

Looking at FIG. 29F, once the sample is collected, the drive motor 184 reverses to rotate the carriage actuation screw 214 in the counterclockwise direction 240. This causes the carriage 186 to retract in direction 240, which in turn causes the lancet 30 to retract from the tissue. As the drive motor 184 continues to retract the carriage 186, the guide pins 226 of the actuator arm 194 move into the first section 234 of the guide slots 230, which in turn disengage the actuator blade 232 from the keyhole 42 in the lancet 30. Before, during or after the actuator arm 194 disengages from the lancet 30, the sensor 174 in the meter 164 can be used to analyze the fluid sample. After the firing mechanism 172 disengages from the lancet 30, the tape 62 can be indexed in the manner as described above so that the now used lancet-sampler 52 can be flipped and wrapped around the spool 116 of the cassette 140, while an unused lancet-sampler 52 is positioned for engagement with the actuator arm 194 of the firing mechanism 172. The drive motor 184 continues to retract the carriage 186 until the collar 220 disengages from the threaded end 218 at the unthreaded section 222 of the carriage screw 214. Around the same time, the clutch 200 of the lancing unit 188 reengages the priming gear 198 so that the drive motor 184 is again able to prime the lancing unit 188. Subsequent lancets 30 are then able to be fired and analyze fluid in the same fashion as described above. It should be recognized that the meters in other embodiments can be configured differently.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. All publications, patents and patent applications cited in this specification are herein incorporated by reference as if each individual publication, patent, or patent application was specifically and individually indicated to be incorporated by reference as set forth in its entirety herein.

What is claimed is:

1. A body fluid sampling device, comprising:
   a lancet including a lancet tip configured to lance tissue;
   a protective cover covering at least a portion of the lancet tip; and
   a tape coupled to the lancet and the protective cover, the tape having a slackened section between the lancet and the protective cover for allowing removal of the protective cover from the lancet tip when the tape is pulled, wherein the slackened section is longer than the distance between where the tape is coupled to the lancet and where the tape is coupled to the protective cover.

2. The device of claim 1, further comprising:
   a test pad for analyzing a body fluid sample disposed on the tape at the slackened section;
   the tape at the slackened section being folded around the test pad to form a packet for protecting the test pad prior to use; and
   the packet being configured to unfold when the tape is pulled.

3. The device of claim 2, wherein:
   the lancet includes a capillary groove extending along the lancet tip for drawing the body fluid sample and a sample transfer opening fluidly coupled to the capillary groove; and
   the test pad is disposed on the tape at a position to align with the sample transfer opening when the packet is unfolded for transferring fluid from the sample transfer opening to the test pad.

4. The device of claim 3, further comprising a cover foil covering at least a portion of the capillary groove to form a closed capillary channel.

5. The device of claim 4, wherein the sample transfer opening has a vent slot that is left uncovered by the cover foil for venting air as the body fluid sample fills the sample transfer opening.

6. The device of claim 3, further comprising:
   the capillary groove being partially etched;
   the sample transfer opening being fully etched;
   the sample transfer opening being wider than the capillary groove; and
   the lancet having a fully etched section having the same width as the capillary groove, the fully etched section being located between the capillary groove and the sample transfer opening to provide a gradual transition between the capillary groove and the sample transfer opening to allow momentum of the body fluid sample to carry the body fluid sample to the sample transfer opening.

7. The device of claim 1, further comprising:
   a first tape connector coupling the protective cover to the tape; and
   a second tape connector coupling the lancet to the tape.

8. The device of claim 1, wherein the lancet defines an actuator engagement opening configured to engage an actuator member of a lancing mechanism to fire the lancet.

9. The device of claim 1, wherein the protective cover includes at least a pair of protective foils between which the lancet tip is sandwiched.

10. The device of claim 1, wherein the slackened section includes a section of the tape that is folded.

11. The device of claim 10, wherein the section of the tape that is folded is folded in a fanfold manner.

12. The device of claim 1, wherein the slackened section is at least long enough for the protective cover to clear the lancet tip.

13. The device of claim 1, further comprising:
   the lancet including a body located opposite the lancet tip;
   the tape being attached to the body of the lancet;
   the tape being attached to the protective cover at the lancet tip; and
   the slackened section of the tape being located between the body and the lancet tip.

14. The device of claim 13, wherein the slackened section includes a section of the tape that is folded.

15. The device of claim 1, wherein the tape and the protective cover are separate components.

16. The device of claim 1, further comprising:
   a spool around which the tape is wrapped.

17. The device of claim 1, wherein the tape is longer than the lancet.

18. The device of claim 1, further comprising:
   a cassette in which the lancet, the protective cover, and the tape is stored, the cassette including
   a storage compartment in which an unused section of the tape is stored, the tape being folded in a fanfold manner inside the storage compartment, and a spool around which the tape is wrapped for indexing the tape.

19. The device of claim 18, further comprising:
the lancet being stored in a tip first orientation when within the storage compartment and a tail first orientation when wrapped around the spool; and
the cassette further including
a guide pin upon which the tape rides between the storage compartment and the spool,
the storage compartment, the guide pin, and the spool being oriented in a triangular relationship in which the tape extends at an acute angle relative to the guide pin, and
a flip wall defining a lancet opening through which the lancet extends during lancing, the flip wall being located between the guide pin and the spool to flip the lancet from the tip first orientation to the tail first orientation when the lancet is indexed from the storage compartment to the spool.

20. The device of claim 19, further comprising:
the lancet having an engagement hole; and
a firing engaging the engagement hole to hold the lancet in place when the protective cover is pulled from the lancet.

21. A body fluid sampling device, comprising:
a lancet configured to lance an incision in tissue; and
a carrier tape coupled to the lancet, wherein the lancet is attached to the carrier tape, the carrier tape including a test pad configured to analyze the body fluid, the tape being folded around the test pad, wherein the tape has a slackened section with the test pad that is located at a position to align with the lancet when the tape is unfolded.

22. The device of claim 21, wherein the lancet defines a capillary groove configured to draw body fluid from the incision via capillary action.

23. The device of claim 22, wherein:
the lancet has a sample transfer opening configured to collect the body fluid from the capillary groove; and
the test pad is located at a position to align with the sample transfer opening when the tape is unfolded.

24. The device of claim 22, further comprising a hydrophilic cover covering at least a portion of the capillary groove to form a closed capillary channel.

25. The device of claim 21, wherein the tape folded around the test pad is sealed together to form an airtight packet.

26. The device of claim 25, wherein the packet is sealed with a peelable adhesive for allowing the tape around the test pad to peel apart.

27. The device of claim 21, further comprising a protective cover covering at least a portion of the lancet, the protective cover being attached to the tape at a position configured to pull the protective cover from the lancet when the tape is pulled.

28. A body fluid sampling device, comprising:
a lancet including
a lancet tip configured to lance tissue,
a body located opposite the lancet tip, and
the lancet defining
a sample transfer opening that extends through opposing sides of the body, and
a capillary groove that extends from the sample transfer opening to the lancet tip for transferring body fluid from the tissue to the sample transfer opening;
a protective cover covering at least a portion of the lancet tip that lances the tissue;
a test pad configured to analyze the body fluid;
a tape having an intermediate section folded around the test pad to form a sealed packet that seals the test pad from exposure to the lancet and the outside environment, the tape being attached to the body of the lancet and the protective cover with the intermediate section having the sealed packet being located in between;
the sealed packet being configured to unfolded when tension is applied to the tape;
the intermediate section being longer that than the distance between the body and the lancet tip when the sealed packet is unfolded to allow the protective cover to pull away from the lancet tip; and
the test pad being positioned on the intermediate section of the tape to align with the sample transfer opening when the sealed packet is unfolded for transferring the body fluid from the sample transfer opening onto the test pad.

29. The device of claim 28, further comprising:
the tape having a first configuration where the test pad is sealed inside the sealed packet and the test pad is out of contact with the sample transfer opening, wherein when in the first configuration the test pad is unable to receive the body fluid from the sample transfer opening;
the tape having a second configuration where the sealed packet is unfolded and the test pad is aligned with the sample transfer opening, wherein when in the second configuration the test pad is able to receive the body fluid from the sample transfer opening; and
the tape being configured to move from the first configuration to the second configuration when the tension is applied to the tape.

30. The device of claim 28, wherein the tape has a plurality of the lancets and test pads.

\* \* \* \* \*